US009572652B2

(12) United States Patent
Cragg et al.

(10) Patent No.: US 9,572,652 B2
(45) Date of Patent: Feb. 21, 2017

(54) MODULAR ENDOGRAFT DEVICES AND ASSOCIATED SYSTEMS AND METHODS

(75) Inventors: Andrew H. Cragg, Edina, MN (US); Stephen Sosnowski, Vista, CA (US); Isa Rizk, San Diego, CA (US); John Fulkerson, Rancho Santa Margarita, CA (US); John Logan, Plymouth, MN (US)

(73) Assignee: Altura Medical, Inc., San Clemente, CA (US)

(*) Notice: Subject to any disclaimer, the term of this patent is extended or adjusted under 35 U.S.C. 154(b) by 0 days.

(21) Appl. No.: 12/958,367

(22) Filed: Dec. 1, 2010

(65) Prior Publication Data

US 2011/0130824 A1 Jun. 2, 2011

Related U.S. Application Data

(60) Provisional application No. 61/265,713, filed on Dec. 1, 2009, provisional application No. 61/293,581, filed
(Continued)

(51) Int. Cl.
*A61F 2/06* (2013.01)
*A61F 2/07* (2013.01)
(Continued)

(52) U.S. Cl.
CPC ...... *A61F 2/07* (2013.01); *A61F 2/89* (2013.01); *A61F 2/90* (2013.01); *A61F 2/95* (2013.01);
(Continued)

(58) Field of Classification Search
CPC ...... A61F 2/07; A61F 2002/8486; A61F 2/90; A61F 2230/0034; A61F 2/89; A61F 2/95;
(Continued)

(56) References Cited

U.S. PATENT DOCUMENTS

| 4,562,596 A | 1/1986 | Kornberg |
| 4,990,151 A | 2/1991 | Wallsten |

(Continued)

FOREIGN PATENT DOCUMENTS

| CN | 1248157 A | 3/2000 |
| CN | 1272053 | 11/2000 |

(Continued)

OTHER PUBLICATIONS

Kahraman, Texas Heart Institute Journal, Diameters of aorta and branches in coronary estasia, pp. 463-468, 2006.*

(Continued)

*Primary Examiner* — Amy R Weisberg
(74) *Attorney, Agent, or Firm* — Craig A. Fieschko, Esq.; DeWitt Ross & Stevens S.C.

(57) ABSTRACT

Modular endograft devices and associated systems and methods are disclosed herein. In several embodiments, an endograft system can include a first endograft device and a second endograft device that each include an integrated frame, a cover and a lumen within the cover. Each endograft device further includes a superior portion and an inferior portion. The superior portion can have a convexly curved outer wall and a septal wall. The first and second endograft devices can be configured to extend into a low-profile configuration with a first cross-sectional dimension and a first length and self-expand into an expanded configuration with a second cross-sectional dimension greater than the first cross-sectional dimension and a second length less than the first length. In the expanded configuration, the septal walls can press against each other and form a septum between the lumens of the first and second endograft devices.

34 Claims, 19 Drawing Sheets

Related U.S. Application Data on Jan. 8, 2010, provisional application No. 61/311,735, filed on Mar. 8, 2010, provisional application No. 61/320,646, filed on Apr. 2, 2010.

(51) Int. Cl.
*A61F 2/95* (2013.01)
*A61F 2/89* (2013.01)
*A61F 2/90* (2013.01)
*A61F 2/848* (2013.01)

(52) U.S. Cl.
CPC ... *A61F 2002/061* (2013.01); *A61F 2002/067* (2013.01); *A61F 2002/072* (2013.01); *A61F 2002/8486* (2013.01); *A61F 2230/0034* (2013.01); *A61F 2250/0039* (2013.01)

(58) Field of Classification Search
CPC .......... A61F 2002/067; A61F 2002/072; A61F 2002/061; A61F 2250/0039
USPC ........ 623/1.11–1.13, 1.35, 1.136, 1.44, 1.16; 606/200
See application file for complete search history.

(56) References Cited

U.S. PATENT DOCUMENTS

| | | |
|---|---|---|
| 5,078,726 A | 1/1992 | Kreamer |
| 5,160,341 A | 11/1992 | Brenneman et al. |
| 5,201,757 A | 4/1993 | Heyn et al. |
| 5,316,023 A | 5/1994 | Palmaz et al. |
| 5,360,443 A | 11/1994 | Barone et al. |
| 5,364,352 A | 11/1994 | Cimino et al. |
| 5,397,345 A | 3/1995 | Lazarus |
| 5,415,664 A | 5/1995 | Pinchuk |
| 5,433,723 A | 7/1995 | Lindenberg et al. |
| 5,445,646 A | 8/1995 | Euteneuer et al. |
| 5,464,449 A | 11/1995 | Ryan et al. |
| 5,476,505 A | 12/1995 | Limon |
| 5,476,506 A | 12/1995 | Lunn |
| 5,480,423 A | 1/1996 | Ravenscroft et al. |
| 5,507,731 A | 4/1996 | Hernandez et al. |
| 5,507,769 A * | 4/1996 | Marin .................. A61F 2/07 604/104 |
| 5,522,880 A | 6/1996 | Barone et al. |
| 5,562,724 A | 10/1996 | Vorwerk et al. |
| 5,571,170 A | 11/1996 | Palmaz et al. |
| 5,571,171 A | 11/1996 | Barone et al. |
| 5,571,173 A | 11/1996 | Parodi |
| 5,575,818 A * | 11/1996 | Pinchuk .................. A61F 2/90 606/195 |
| 5,578,071 A | 11/1996 | Parodi |
| 5,578,072 A | 11/1996 | Barone et al. |
| 5,591,195 A | 1/1997 | Taheri et al. |
| 5,591,228 A | 1/1997 | Edoga |
| 5,591,229 A | 1/1997 | Parodi |
| 5,609,627 A | 3/1997 | Goicoechea et al. |
| 5,626,604 A | 5/1997 | Cottone, Jr. |
| 5,628,783 A | 5/1997 | Quiachon et al. |
| 5,628,788 A | 5/1997 | Pinchuk |
| 5,632,763 A | 5/1997 | Glastra |
| 5,632,772 A | 5/1997 | Alcime et al. |
| 5,639,278 A | 6/1997 | Dereume et al. |
| 5,653,743 A | 8/1997 | Martin |
| 5,662,606 A | 9/1997 | Cimino et al. |
| 5,683,450 A | 11/1997 | Goicoechea et al. |
| 5,683,453 A | 11/1997 | Palmaz |
| 5,693,084 A | 12/1997 | Chuter |
| 5,693,087 A | 12/1997 | Parodi |
| 5,707,376 A | 1/1998 | Kavteladze et al. |
| 5,713,917 A | 2/1998 | Leonhardt et al. |
| 5,716,365 A | 2/1998 | Goicoechea et al. |
| 5,755,734 A | 5/1998 | Richter et al. |
| 5,755,735 A | 5/1998 | Richter et al. |
| 5,755,770 A | 5/1998 | Ravenscroft |
| 5,759,186 A | 6/1998 | Bachmann et al. |
| 5,776,142 A | 7/1998 | Gunderson |
| 5,817,102 A | 10/1998 | Johnson et al. |
| 5,824,041 A | 10/1998 | Lenker et al. |
| 5,824,058 A | 10/1998 | Ravenscroft et al. |
| 5,833,694 A | 11/1998 | Poncet |
| 5,843,160 A | 12/1998 | Rhodes |
| 5,855,598 A | 1/1999 | Pinchuk |
| 5,871,536 A | 2/1999 | Lazarus |
| 5,888,201 A | 3/1999 | Stinson et al. |
| 5,897,587 A | 4/1999 | Martakos et al. |
| 5,904,713 A | 5/1999 | Leschinsky |
| 5,906,619 A | 5/1999 | Olson et al. |
| 5,916,263 A | 6/1999 | Goicoechea et al. |
| 5,928,279 A | 7/1999 | Shannon et al. |
| 5,968,068 A | 10/1999 | Dehdashtian et al. |
| 5,984,955 A | 11/1999 | Wisselink |
| 5,984,964 A | 11/1999 | Roberts et al. |
| 5,993,481 A | 11/1999 | Marcade et al. |
| 6,001,125 A | 12/1999 | Golds et al. |
| 6,004,348 A | 12/1999 | Banas et al. |
| 6,015,431 A | 1/2000 | Thornton et al. |
| 6,019,778 A | 2/2000 | Wilson et al. |
| 6,024,763 A | 2/2000 | Lenker et al. |
| 6,039,749 A * | 3/2000 | Marin .................. A61F 2/07 604/103.07 |
| 6,042,589 A | 3/2000 | Marianne |
| 6,051,020 A | 4/2000 | Goicoechea et al. |
| 6,053,899 A | 4/2000 | Slanda et al. |
| 6,060,128 A | 5/2000 | Kim et al. |
| 6,070,589 A * | 6/2000 | Keith et al. ................... 128/898 |
| 6,077,296 A | 6/2000 | Shokoohi et al. |
| 6,090,128 A | 7/2000 | Douglas |
| 6,090,133 A | 7/2000 | Richter et al. |
| 6,099,558 A | 8/2000 | White et al. |
| 6,102,940 A | 8/2000 | Robichon et al. |
| 6,117,156 A | 9/2000 | Richter et al. |
| 6,117,167 A | 9/2000 | Goicoechea et al. |
| 6,120,522 A | 9/2000 | Vrba et al. |
| 6,126,685 A | 10/2000 | Lenker et al. |
| 6,129,756 A | 10/2000 | Kugler et al. |
| 6,146,415 A | 11/2000 | Fitz |
| 6,156,063 A | 12/2000 | Douglas |
| 6,162,237 A | 12/2000 | Chan |
| 6,162,246 A | 12/2000 | Barone |
| 6,165,213 A | 12/2000 | Goicoechea et al. |
| 6,168,610 B1 | 1/2001 | Marin et al. |
| 6,168,616 B1 | 1/2001 | Brown, III |
| 6,171,277 B1 | 1/2001 | Ponzi |
| 6,174,330 B1 | 1/2001 | Stinson |
| 6,179,809 B1 | 1/2001 | Khairkhahan et al. |
| 6,183,444 B1 | 2/2001 | Glines et al. |
| 6,183,481 B1 | 2/2001 | Lee et al. |
| 6,187,036 B1 | 2/2001 | Shaolian et al. |
| 6,190,360 B1 | 2/2001 | Iancea et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,210,422 B1 | 4/2001 | Douglas |
| 6,217,609 B1 | 4/2001 | Haverkost |
| 6,221,102 B1 | 4/2001 | Baker et al. |
| 6,230,476 B1 | 5/2001 | Carr et al. |
| 6,231,597 B1 | 5/2001 | Deem et al. |
| 6,238,402 B1 | 5/2001 | Sullivan, III et al. |
| 6,261,316 B1 | 7/2001 | Shaolian et al. |
| 6,267,783 B1 * | 7/2001 | Letendre .................. A61F 2/07 623/1.11 |
| 6,270,525 B1 | 8/2001 | Letendre et al. |
| 6,290,731 B1 | 9/2001 | Solovay et al. |
| 6,302,906 B1 | 10/2001 | Goicoechea et al. |
| 6,306,141 B1 | 10/2001 | Jervis |
| 6,306,164 B1 | 10/2001 | Kujawski |
| 6,306,424 B1 | 10/2001 | Vyakarnam et al. |
| 6,309,413 B1 | 10/2001 | Dereume et al. |
| 6,325,819 B1 | 12/2001 | Pavcnik et al. |
| 6,325,822 B1 | 12/2001 | Chouinard et al. |
| 6,331,190 B1 | 12/2001 | Shokoohi et al. |
| 6,331,191 B1 | 12/2001 | Chobotov |

(56) References Cited

U.S. PATENT DOCUMENTS

| | | | |
|---|---|---|---|
| 6,344,052 B1 | 2/2002 | Greenan et al. | |
| 6,344,056 B1 * | 2/2002 | Dehdashtian | A61F 2/07 623/1.35 |
| 6,371,963 B1 | 4/2002 | Nishtala et al. | |
| 6,383,193 B1 | 5/2002 | Cathcart et al. | |
| 6,391,033 B2 | 5/2002 | Ryan | |
| 6,391,051 B2 | 5/2002 | Sullivan, III et al. | |
| 6,395,019 B2 | 5/2002 | Chobotov | |
| 6,398,802 B1 | 6/2002 | Yee | |
| 6,398,807 B1 | 6/2002 | Chouinard et al. | |
| 6,409,750 B1 | 6/2002 | Hyodoh et al. | |
| 6,413,269 B1 | 7/2002 | Bui et al. | |
| 6,416,542 B1 | 7/2002 | Marcade et al. | |
| 6,468,260 B1 | 10/2002 | Bumbalough et al. | |
| 6,478,813 B1 * | 11/2002 | Keith | A61F 2/07 128/898 |
| 6,482,227 B1 | 11/2002 | Solovay | |
| 6,488,700 B2 | 12/2002 | Klumb et al. | |
| 6,500,203 B1 | 12/2002 | Thompson et al. | |
| 6,514,261 B1 | 2/2003 | Randall et al. | |
| 6,517,571 B1 | 2/2003 | Brauker et al. | |
| 6,517,572 B2 | 2/2003 | Kugler et al. | |
| 6,517,574 B1 | 2/2003 | Chuter | |
| 6,520,983 B1 | 2/2003 | Colgan et al. | |
| 6,524,336 B1 | 2/2003 | Papazolgou et al. | |
| 6,533,811 B1 | 3/2003 | Ryan et al. | |
| 6,554,794 B1 | 4/2003 | Mueller et al. | |
| 6,554,858 B2 | 4/2003 | Dereume et al. | |
| RE38,146 E | 6/2003 | Palmaz et al. | |
| 6,572,643 B1 | 6/2003 | Gharibadeh | |
| 6,576,006 B2 | 6/2003 | Limon et al. | |
| 6,585,756 B1 | 7/2003 | Strecker | |
| 6,602,225 B2 | 8/2003 | Eidenschink et al. | |
| 6,602,280 B2 | 8/2003 | Chobotov | |
| 6,629,981 B2 | 10/2003 | Bui et al. | |
| 6,645,242 B1 | 11/2003 | Quinn | |
| 6,652,567 B1 * | 11/2003 | Deaton | A61F 2/07 623/1.1 |
| 6,656,215 B1 | 12/2003 | Yanez et al. | |
| 6,660,030 B2 | 12/2003 | Shaolian et al. | |
| 6,663,645 B2 | 12/2003 | Nishtala et al. | |
| 6,669,716 B1 | 12/2003 | Gilson et al. | |
| 6,682,557 B1 | 1/2004 | Quiachon et al. | |
| 6,695,875 B2 | 2/2004 | Stelter et al. | |
| 6,730,119 B1 * | 5/2004 | Smalling | 623/1.35 |
| 6,733,521 B2 | 5/2004 | Chobotov et al. | |
| 6,743,247 B1 | 6/2004 | Levinson et al. | |
| 6,755,854 B2 | 6/2004 | Gillick et al. | |
| 6,761,733 B2 | 7/2004 | Chobotov et al. | |
| 6,773,454 B2 * | 8/2004 | Wholey | A61F 2/07 623/1.15 |
| 6,773,457 B2 | 8/2004 | Ivancev et al. | |
| 6,786,920 B2 | 9/2004 | Shannon et al. | |
| 6,790,225 B1 | 9/2004 | Shannon et al. | |
| 6,792,979 B2 | 9/2004 | Konya et al. | |
| 6,808,529 B2 | 10/2004 | Fulkerson | |
| 6,808,533 B1 | 10/2004 | Goodwin et al. | |
| 6,808,534 B1 | 10/2004 | Escano | |
| 6,814,752 B1 | 11/2004 | Chuter | |
| 6,830,575 B2 | 12/2004 | Stenzel et al. | |
| 6,843,802 B1 | 1/2005 | Villalobos et al. | |
| 6,843,803 B2 | 1/2005 | Ryan et al. | |
| 6,849,084 B2 | 2/2005 | Rabkin et al. | |
| 6,858,038 B2 | 2/2005 | Heuser | |
| 6,866,669 B2 | 3/2005 | Buzzard et al. | |
| 6,878,164 B2 | 4/2005 | Kujawski et al. | |
| 6,887,268 B2 * | 5/2005 | Butaric | A61F 2/064 623/1.16 |
| 6,911,039 B2 | 6/2005 | Shiu et al. | |
| 6,913,594 B2 | 7/2005 | Coleman et al. | |
| 6,926,724 B1 | 8/2005 | Chu | |
| 6,929,661 B2 | 8/2005 | Bolduc et al. | |
| 6,939,352 B2 | 9/2005 | Buzzard et al. | |
| 6,939,371 B2 | 9/2005 | Kugler et al. | |
| 6,942,691 B1 | 9/2005 | Chuter | |
| 6,942,692 B2 | 9/2005 | Landau et al. | |
| 6,951,572 B1 | 10/2005 | Douglas | |
| 6,964,679 B1 | 11/2005 | Marcade et al. | |
| 6,974,471 B2 | 12/2005 | Van Schie et al. | |
| 6,981,982 B2 | 1/2006 | Armstrong et al. | |
| 6,984,243 B2 | 1/2006 | Dwyer et al. | |
| 6,984,244 B2 | 1/2006 | Perez et al. | |
| 7,000,649 B2 | 2/2006 | Takahashi et al. | |
| 7,001,423 B2 | 2/2006 | Euteneuer et al. | |
| 7,014,653 B2 * | 3/2006 | Ouriel et al. | 623/1.14 |
| 7,018,401 B1 | 3/2006 | Hyodoh et al. | |
| 7,048,014 B2 | 5/2006 | Hyodoh et al. | |
| 7,052,511 B2 | 5/2006 | Weldon et al. | |
| 7,052,513 B2 | 5/2006 | Thompson | |
| 7,063,721 B2 | 6/2006 | Takahashi et al. | |
| 7,074,236 B2 | 7/2006 | Rabkin et al. | |
| 7,105,016 B2 | 9/2006 | Shiu et al. | |
| 7,112,217 B1 * | 9/2006 | Kugler | A61F 2/07 623/1.13 |
| 7,118,592 B1 | 10/2006 | Dang et al. | |
| 7,122,050 B2 | 10/2006 | Randall et al. | |
| 7,122,052 B2 * | 10/2006 | Greenhalgh | A61F 2/07 623/1.13 |
| 7,131,991 B2 | 11/2006 | Zarins et al. | |
| 7,144,421 B2 | 12/2006 | Carpenter et al. | |
| 7,147,656 B2 | 12/2006 | Andreas et al. | |
| 7,160,318 B2 | 1/2007 | Greenberg et al. | |
| 7,169,118 B2 | 1/2007 | Reynolds et al. | |
| 7,175,651 B2 | 2/2007 | Kerr | |
| 7,220,274 B1 | 5/2007 | Quinn | |
| 7,226,474 B2 * | 6/2007 | Iancea | A61F 2/07 623/1.13 |
| 7,229,472 B2 * | 6/2007 | DePalma | A61F 2/064 623/1.16 |
| 7,232,459 B2 | 6/2007 | Greenberg et al. | |
| 7,238,197 B2 | 7/2007 | Sequin et al. | |
| 7,264,631 B2 | 9/2007 | DiCarlo | |
| 7,264,632 B2 | 9/2007 | Wright et al. | |
| 7,267,685 B2 | 9/2007 | Butaric et al. | |
| 7,278,998 B2 | 10/2007 | Gaschino et al. | |
| 7,294,147 B2 | 11/2007 | Hartley | |
| 7,306,623 B2 | 12/2007 | Watson | |
| 7,314,483 B2 * | 1/2008 | Landau | A61F 2/064 623/1.16 |
| 7,314,484 B2 * | 1/2008 | Deem | A61F 2/07 623/1.36 |
| 7,318,835 B2 | 1/2008 | Berra | |
| 7,326,237 B2 | 2/2008 | DePalma et al. | |
| 7,344,562 B2 | 3/2008 | Feller et al. | |
| 7,357,812 B2 | 4/2008 | Andreas et al. | |
| 7,371,255 B2 | 5/2008 | Richter et al. | |
| RE40,404 E | 6/2008 | Schmitt et al. | |
| 7,402,163 B2 | 7/2008 | Nishtala et al. | |
| 7,435,253 B1 | 10/2008 | Hartley et al. | |
| 7,476,244 B2 | 1/2009 | Buzzard et al. | |
| 7,481,836 B2 | 1/2009 | Greenan | |
| 7,488,344 B2 | 2/2009 | Hartley et al. | |
| 7,517,361 B1 | 4/2009 | Ravenscroft | |
| RE40,816 E | 6/2009 | Taylor et al. | |
| 7,550,004 B2 | 6/2009 | Bahler et al. | |
| 7,575,591 B2 | 8/2009 | Howat et al. | |
| 7,588,596 B2 | 9/2009 | Spiridigliozzi et al. | |
| 7,615,044 B2 | 11/2009 | Scheibe et al. | |
| 7,615,071 B2 | 11/2009 | Chobotov | |
| 7,637,932 B2 * | 12/2009 | Bolduc et al. | 623/1.11 |
| 7,655,034 B2 | 2/2010 | Mitchell et al. | |
| 7,655,040 B2 | 2/2010 | Douk et al. | |
| 7,666,220 B2 * | 2/2010 | Evans | A61B 17/12118 623/1.25 |
| 7,674,282 B2 | 3/2010 | Wu et al. | |
| 7,678,141 B2 | 3/2010 | Greenan et al. | |
| 7,682,381 B2 | 3/2010 | Rakos et al. | |
| 7,691,109 B2 | 4/2010 | Armstrong et al. | |
| 7,691,138 B2 | 4/2010 | Stenzel et al. | |
| 7,695,506 B2 | 4/2010 | Thistle et al. | |
| 7,708,771 B2 * | 5/2010 | Chuter | A61F 2/07 623/1.13 |

(56) References Cited

U.S. PATENT DOCUMENTS

| | | | |
|---|---|---|---|
| 7,766,960 B2 | 8/2010 | Alexander et al. | |
| 7,766,961 B2 | 8/2010 | Patel et al. | |
| 7,780,717 B2 | 8/2010 | Ducke et al. | |
| 7,828,833 B2 | 11/2010 | Haverkost et al. | |
| 7,828,838 B2* | 11/2010 | Bolduc et al. | 623/1.36 |
| 7,837,724 B2 | 11/2010 | Keeble et al. | |
| 7,862,609 B2 | 1/2011 | Butaric et al. | |
| 7,887,576 B2 | 2/2011 | Bahler et al. | |
| 7,918,880 B2 | 4/2011 | Austin | |
| 7,935,140 B2 | 5/2011 | Griffin | |
| 7,938,852 B2 | 5/2011 | Andreas et al. | |
| 7,993,384 B2 | 8/2011 | Wu et al. | |
| 8,021,410 B2 | 9/2011 | Melsheimer | |
| 8,025,692 B2 | 9/2011 | Feeser | |
| 8,075,606 B2 | 12/2011 | Dorn | |
| 8,080,050 B2 | 12/2011 | Chiang et al. | |
| 8,114,147 B2* | 2/2012 | Wood | A61F 2/90 623/1.15 |
| 8,136,004 B2 | 3/2012 | Umesh et al. | |
| 8,163,004 B2 | 4/2012 | Amplatz et al. | |
| 8,163,006 B2* | 4/2012 | Feller et al. | 623/1.35 |
| 8,164,892 B2 | 4/2012 | An | |
| 8,167,892 B2 | 5/2012 | Feller, III et al. | |
| 8,187,291 B2 | 5/2012 | Nishtala et al. | |
| 8,241,344 B2 | 8/2012 | Kusleika et al. | |
| 8,287,583 B2 | 10/2012 | LaDuca et al. | |
| 8,323,239 B2 | 12/2012 | Bednarek et al. | |
| 8,357,190 B2 | 1/2013 | Fearn et al. | |
| 8,372,131 B2 | 2/2013 | Hestad et al. | |
| 8,434,393 B2 | 5/2013 | Adams | |
| 8,470,015 B2 | 6/2013 | Barthold | |
| 8,486,128 B2 | 7/2013 | Jen et al. | |
| 2001/0014823 A1 | 8/2001 | Ressemann et al. | |
| 2002/0013620 A1 | 1/2002 | Kujawski | |
| 2002/0019659 A1 | 2/2002 | Goicoechea et al. | |
| 2002/0019664 A1 | 2/2002 | Douglas | |
| 2002/0143387 A1* | 10/2002 | Soetikno et al. | 623/1.15 |
| 2002/0151933 A1 | 10/2002 | Sheldon | |
| 2002/0169497 A1 | 11/2002 | Wholey et al. | |
| 2003/0014075 A1 | 1/2003 | Rosenbluth et al. | |
| 2003/0130720 A1 | 7/2003 | DePalma et al. | |
| 2003/0130725 A1* | 7/2003 | DePalma | A61F 2/07 623/1.16 |
| 2003/0199967 A1 | 10/2003 | Hartley et al. | |
| 2003/0199973 A1 | 10/2003 | Chuter et al. | |
| 2004/0019375 A1 | 1/2004 | Casey et al. | |
| 2004/0054397 A1 | 3/2004 | Smith et al. | |
| 2004/0059406 A1 | 3/2004 | Cully et al. | |
| 2004/0073288 A1 | 4/2004 | Kerr | |
| 2004/0082989 A1* | 4/2004 | Cook | A61F 2/07 623/1.13 |
| 2004/0098092 A1 | 5/2004 | Butaric et al. | |
| 2004/0117003 A1 | 6/2004 | Ouriel et al. | |
| 2004/0138734 A1 | 7/2004 | Chobotov et al. | |
| 2004/0143316 A1 | 7/2004 | Spiridigliozzi et al. | |
| 2004/0162604 A1 | 8/2004 | Sowinski et al. | |
| 2004/0167599 A1 | 8/2004 | Goicoechea et al. | |
| 2004/0193245 A1* | 9/2004 | Deem | A61F 2/07 623/1.13 |
| 2004/0193252 A1 | 9/2004 | Perez et al. | |
| 2004/0215316 A1 | 10/2004 | Smalling | |
| 2004/0230289 A1 | 11/2004 | DiMatteo et al. | |
| 2004/0236406 A1 | 11/2004 | Gregorich | |
| 2004/0260382 A1 | 12/2004 | Fogarty et al. | |
| 2005/0015441 A1 | 1/2005 | Attwood et al. | |
| 2005/0021123 A1 | 1/2005 | Dorn et al. | |
| 2005/0033400 A1 | 2/2005 | Chuter | |
| 2005/0033416 A1 | 2/2005 | Seguin et al. | |
| 2005/0043780 A1 | 2/2005 | Gifford et al. | |
| 2005/0049607 A1 | 3/2005 | Hart et al. | |
| 2005/0085894 A1 | 4/2005 | Kershner | |
| 2005/0113906 A9 | 5/2005 | Bolduc et al. | |
| 2005/0119721 A1 | 6/2005 | Rabkin et al. | |
| 2005/0131516 A1 | 6/2005 | Greenhalgh | |
| 2005/0137677 A1* | 6/2005 | Rush | 623/1.13 |
| 2005/0143804 A1 | 6/2005 | Haverkost | |
| 2005/0154441 A1 | 7/2005 | Schaeffer et al. | |
| 2005/0171598 A1 | 8/2005 | Schaeffer | |
| 2005/0222668 A1 | 10/2005 | Schaeffer et al. | |
| 2005/0228475 A1 | 10/2005 | Keeble et al. | |
| 2005/0228484 A1 | 10/2005 | Stephens et al. | |
| 2005/0240258 A1* | 10/2005 | Bolduc et al. | 623/1.27 |
| 2005/0273154 A1 | 12/2005 | Colone | |
| 2005/0288772 A1 | 12/2005 | Douglas | |
| 2006/0030921 A1 | 2/2006 | Chu | |
| 2006/0058864 A1 | 3/2006 | Schaeffer et al. | |
| 2006/0069323 A1* | 3/2006 | Elkins et al. | 600/585 |
| 2006/0074481 A1* | 4/2006 | Vardi | A61F 2/07 623/1.36 |
| 2006/0085057 A1 | 4/2006 | George et al. | |
| 2006/0095116 A1 | 5/2006 | Bolduc et al. | |
| 2006/0142694 A1 | 6/2006 | Bednarek et al. | |
| 2006/0155359 A1 | 7/2006 | Watson | |
| 2006/0155366 A1 | 7/2006 | LaDuca et al. | |
| 2006/0161244 A1 | 7/2006 | Seguin | |
| 2006/0178733 A1 | 8/2006 | Pinchuk et al. | |
| 2006/0212112 A1* | 9/2006 | Evans | A61F 2/07 623/1.25 |
| 2006/0224232 A1 | 10/2006 | Chobotov | |
| 2006/0233990 A1 | 10/2006 | Humphrey et al. | |
| 2006/0265055 A1 | 11/2006 | Lauterjung | |
| 2006/0282155 A1 | 12/2006 | Fearn et al. | |
| 2007/0032852 A1 | 2/2007 | Machek et al. | |
| 2007/0051377 A1 | 3/2007 | Douk et al. | |
| 2007/0055341 A1 | 3/2007 | Edoga et al. | |
| 2007/0055360 A1 | 3/2007 | Hanson et al. | |
| 2007/0055363 A1 | 3/2007 | Chuter et al. | |
| 2007/0100429 A1 | 5/2007 | Wu et al. | |
| 2007/0112415 A1* | 5/2007 | Bartlett | A61F 2/90 623/1.15 |
| 2007/0118208 A1 | 5/2007 | Kerr | |
| 2007/0142895 A1 | 6/2007 | Castaneda et al. | |
| 2007/0142896 A1 | 6/2007 | Anderson et al. | |
| 2007/0150041 A1 | 6/2007 | Evans et al. | |
| 2007/0156224 A1 | 7/2007 | Cioanta et al. | |
| 2007/0156229 A1 | 7/2007 | Park | |
| 2007/0162109 A1 | 7/2007 | Davila et al. | |
| 2007/0168017 A1 | 7/2007 | Sarac | |
| 2007/0168018 A1 | 7/2007 | Amplatz et al. | |
| 2007/0173729 A1 | 7/2007 | Boucher et al. | |
| 2007/0179592 A1 | 8/2007 | Schaeffer | |
| 2007/0179600 A1 | 8/2007 | Vardi | |
| 2007/0198077 A1 | 8/2007 | Cully et al. | |
| 2007/0198079 A1 | 8/2007 | Casey et al. | |
| 2007/0219620 A1 | 9/2007 | Eells et al. | |
| 2007/0225797 A1 | 9/2007 | Krivoruhko | |
| 2007/0233220 A1 | 10/2007 | Greenan | |
| 2007/0233222 A1 | 10/2007 | Roeder et al. | |
| 2007/0244542 A1 | 10/2007 | Greenan et al. | |
| 2007/0244547 A1 | 10/2007 | Greenan | |
| 2007/0265697 A1 | 11/2007 | Goicoechea et al. | |
| 2007/0293940 A1 | 12/2007 | Schaeffer et al. | |
| 2008/0015682 A1 | 1/2008 | Majercak et al. | |
| 2008/0046065 A1 | 2/2008 | Hartley et al. | |
| 2008/0082154 A1 | 4/2008 | Tseng et al. | |
| 2008/0082158 A1 | 4/2008 | Tseng et al. | |
| 2008/0082159 A1 | 4/2008 | Tseng et al. | |
| 2008/0097572 A1 | 4/2008 | Sheldon et al. | |
| 2008/0108969 A1 | 5/2008 | Kerr | |
| 2008/0114435 A1 | 5/2008 | Bowe | |
| 2008/0114444 A1 | 5/2008 | Yu | |
| 2008/0114449 A1 | 5/2008 | Gregorich et al. | |
| 2008/0125847 A1 | 5/2008 | Krever et al. | |
| 2008/0132993 A1 | 6/2008 | Rasmussen et al. | |
| 2008/0167704 A1 | 7/2008 | Wright et al. | |
| 2008/0183272 A1 | 7/2008 | Wood et al. | |
| 2008/0195191 A1 | 8/2008 | Luo et al. | |
| 2008/0208325 A1 | 8/2008 | Helmus et al. | |
| 2008/0221659 A1 | 9/2008 | Hartley et al. | |
| 2008/0221668 A1 | 9/2008 | Pinchuk et al. | |
| 2008/0249601 A1 | 10/2008 | Kerr | |
| 2008/0262595 A1 | 10/2008 | Chu et al. | |
| 2008/0290076 A1 | 11/2008 | Sheldon et al. | |
| 2009/0030501 A1 | 1/2009 | Morris et al. | |

(56) References Cited

U.S. PATENT DOCUMENTS

| | | |
|---|---|---|
| 2009/0036973 A1 | 2/2009 | Humphrey et al. |
| 2009/0043376 A1 | 2/2009 | Hamer et al. |
| 2009/0099647 A1 | 4/2009 | Glimsdale et al. |
| 2009/0099649 A1 | 4/2009 | Chobotov et al. |
| 2009/0105640 A1 | 4/2009 | Bednarek et al. |
| 2009/0125095 A1* | 5/2009 | Bui .................. A61F 2/07 623/1.13 |
| 2009/0138067 A1 | 5/2009 | Pinchuk et al. |
| 2009/0164001 A1 | 6/2009 | Biggs et al. |
| 2009/0171451 A1 | 7/2009 | Kuppurathanam et al. |
| 2009/0173439 A1 | 7/2009 | Hayashi et al. |
| 2009/0177265 A1 | 7/2009 | Dierking et al. |
| 2009/0182413 A1 | 7/2009 | Burkart et al. |
| 2009/0187240 A1* | 7/2009 | Clerc ................ A61F 2/07 623/1.17 |
| 2009/0198267 A1* | 8/2009 | Evans ................ A61F 2/07 606/195 |
| 2009/0228020 A1 | 9/2009 | Wallace et al. |
| 2009/0248144 A1 | 10/2009 | Bahler et al. |
| 2009/0264992 A1 | 10/2009 | Fleming, III et al. |
| 2009/0276035 A1 | 11/2009 | Waysbeyn et al. |
| 2009/0287145 A1 | 11/2009 | Cragg et al. |
| 2009/0318949 A1* | 12/2009 | Ganpath ............ A61F 2/07 606/192 |
| 2009/0319029 A1* | 12/2009 | Evans ................ A61F 2/07 623/1.35 |
| 2010/0004728 A1* | 1/2010 | Rao .................. A61F 2/07 623/1.11 |
| 2010/0030255 A1 | 2/2010 | Berra et al. |
| 2010/0030321 A1* | 2/2010 | Mach ................ A61F 2/07 623/1.18 |
| 2010/0036360 A1* | 2/2010 | Herbowy ........ A61B 17/12118 604/500 |
| 2010/0049291 A1 | 2/2010 | Yampolsky et al. |
| 2010/0094394 A1 | 4/2010 | Beach et al. |
| 2010/0094400 A1* | 4/2010 | Bolduc et al. ............. 623/1.11 |
| 2010/0094403 A1* | 4/2010 | Heraty ............... A61F 2/958 623/1.15 |
| 2010/0100167 A1 | 4/2010 | Bortlein et al. |
| 2010/0106239 A1 | 4/2010 | Roeder |
| 2010/0262216 A1 | 10/2010 | Xue |
| 2010/0286756 A1 | 11/2010 | Dorn et al. |
| 2010/0292771 A1* | 11/2010 | Paskar ............... A61F 2/954 623/1.11 |
| 2010/0305686 A1 | 12/2010 | Cragg et al. |
| 2011/0022149 A1 | 1/2011 | Cox et al. |
| 2011/0079315 A1* | 4/2011 | Norton et al. ............. 140/71 R |
| 2011/0125248 A1 | 5/2011 | George et al. |
| 2011/0178589 A1 | 7/2011 | Andreas et al. |
| 2011/0213450 A1 | 9/2011 | Maclean et al. |
| 2011/0257673 A1* | 10/2011 | Heraty et al. ................. 606/194 |
| 2011/0257720 A1 | 10/2011 | Peterson et al. |
| 2011/0264074 A1 | 10/2011 | Tegg et al. |
| 2011/0295354 A1 | 12/2011 | Bueche et al. |
| 2011/0313505 A1 | 12/2011 | McHugo |
| 2012/0041536 A1 | 2/2012 | Hansen |
| 2012/0130469 A1 | 5/2012 | Cragg et al. |
| 2012/0158115 A9 | 6/2012 | Arnault De La Menardiere et al. |
| 2012/0158117 A1 | 6/2012 | Ryan |
| 2012/0165919 A1 | 6/2012 | Cox et al. |
| 2012/0172968 A1 | 7/2012 | Chuter et al. |
| 2012/0185031 A1 | 7/2012 | Ryan et al. |
| 2012/0197376 A1 | 8/2012 | Heidner et al. |
| 2012/0209063 A1 | 8/2012 | Nishtala et al. |
| 2012/0221091 A1 | 8/2012 | Hartly et al. |
| 2012/0221093 A1 | 8/2012 | McHugo |
| 2012/0330398 A1 | 12/2012 | Hyodoh et al. |
| 2013/0035749 A1 | 2/2013 | Farag |
| 2013/0096407 A1 | 4/2013 | Bednarek et al. |
| 2013/0123898 A1 | 5/2013 | Tung et al. |
| 2013/0131774 A1 | 5/2013 | Nabulsi et al. |
| 2014/0046428 A1 | 2/2014 | Cragg et al. |
| 2014/0046429 A1 | 2/2014 | Cragg et al. |

FOREIGN PATENT DOCUMENTS

| | | |
|---|---|---|
| EP | 808613 A1 | 11/1997 |
| EP | 971646 B1 | 1/2000 |
| EP | 1803418 A1 | 7/2007 |
| FR | 2743293 | 7/1997 |
| JP | A-H08-50141 | 2/1996 |
| JP | A-H10-507382 | 7/1998 |
| JP | A-2009-504349 | 2/1999 |
| JP | A-H11-50143 | 2/1999 |
| JP | A-2000-185105 | 7/2000 |
| JP | A-2008-518710 | 6/2008 |
| JP | A-2008-539050 | 11/2008 |
| WO | WO-9319703 | 10/1993 |
| WO | WO-9632077 A1 | 10/1996 |
| WO | WO-9852496 | 11/1998 |
| WO | WO-9855047 A1 | 12/1998 |
| WO | WO-0105332 A1 | 1/2001 |
| WO | WO-0152770 A1 | 7/2001 |
| WO | WO-03084439 | 10/2003 |
| WO | WO-2005112823 | 12/2005 |
| WO | WO-2006116725 | 11/2006 |
| WO | WO-2008005535 | 1/2008 |
| WO | WO-2009132309 | 10/2009 |
| WO | WO-2009/140638 A1 | 11/2009 |
| WO | WO-2010/132836 A2 | 11/2010 |
| WO | WO-PCT/US10/58621 | 12/2010 |
| WO | WO-2011003019 A1 | 1/2011 |
| WO | WO-2011049808 | 4/2011 |
| WO | WO2012040240 | 3/2012 |
| WO | WO-2012128846 | 9/2012 |

OTHER PUBLICATIONS

U.S. Appl. No. 61/053,378, filed May 15, 2008, Cragg et al.
U.S. Appl. No. 61/265,713, filed Dec. 1, 2009, Cragg et al.
U.S. Appl. No. 12/958,374, filed Dec. 1, 2010, Cragg et al.
U.S. Appl. No. 12/958,378, filed Dec. 1, 2010, Cragg et al.
U.S. Appl. No. 12/958,381, filed Dec. 1, 2010, Cragg et al.
U.S. Appl. No. 12/958,383, filed Dec. 1, 2010, Cragg et al.
U.S. Appl. No. 61/293,581, filed Jan. 8, 2010, Cragg et al.
U.S. Appl. No. 61/311,735, filed Mar. 8, 2010, Cragg et al.
U.S. Appl. No. 61/320,646, filed Apr. 2, 2010, Cragg et al.
U.S. Appl. No. 61/384,669, filed Sep. 20, 2010, Cragg et al.
International Search Report and Written Opinion, PCT/US09/44212, Mailed on Jul. 14, 2009, Applicant: Altura Medical, Inc., 11 pages.
International Search Report and Written Opinion, PCT/US10/58621, Mailed on Feb. 9, 2011, Applicant: Altura Medical, Inc., 34 pages.
U.S. Appl. No. 12/628,131, filed Nov. 30, 2009, Cragg et al.
Laborde, Jean Claude et al., "A Novel 14F Endograft for Abdominal Aortic Aneurysm: First in Man," Catheterization and Cardiovascular Interventions, Jun. 2010 (20 pages).
Beebe, H.G.; "Imaging Modalities for Aortic Endografting"; J Endovasc Surg; May 1997; vol. 4, Issue 2, pp. 111-123 (20 pages).
Brewster, DC; "Initial Experience with Endovascular Aneurysm Repair: Comparison of Early Results with Outcome of Conventional Open Repair"; J Vasc Surg; Jun. 1998; vol. 27, Issue 6, pp. 992-1003; discussion 1004-5 (14 pages).
Cao, P.; "*Comparison of Surveillance* vs *Aortic Endografting for Small Aneurysm Repair (CAESAR)* Trial: Study Design and Progress"; Eur. J. Vasc. Endovasc. Surg.; Sep. 2005; vol. 30, Issue 3; pp. 245-251 (7 pages).
Dorros, G. et al.; "Evaluation of Endovascular Abdominal Aortic Aneurysm Repair: Anatomical Classicication, Procedural Success, Clinical Assessment, and Data Collection"; J. Endovasc Surg; May 1997; vol. 4, Issue 2; pp. 203-225 (24 pages).
Dosluoglu et al.; "Total Percutaneous Endovascular Repair of Abdominal Aortic Aneurysms Using Perclose ProGlide Closure Devices"; J. Endovasc Ther.; Apr. 2007, vol. 14, Issue 2, pp. 184-188 (5 pages).
Faries, PL; "Endovascular Stent Graft Selection for the Treatment of Abdominal Aortic Aneurysms"; J. Cardiovasc Surg (Torino); Feb. 2005; vol. 46, Issue 1, pp. 9-17 (9 pages).

(56) References Cited

OTHER PUBLICATIONS

International Search Report and Written Opinion, PCT/US2011/052412, Mailed on Jan. 17, 2012, Applicant: Altura Medical, Inc., 9 pages.

Mathison, MN; "Implications of Problematic Access in Transluminal Endografting of Abdominal Aortic Aneurysm"; J Vasc Interv Radiol; Jan. 2003; vol. 14, Issue 1, pp. 33-39 (7 pages).

Matsumura, JS; "A Multicenter Controlled Clinical Trial of Open Versus Endovascular Treatment of Abdominal Aortic Aneurysm"; J Vasc Surg; Feb. 2003; vol. 37, Issue 2, pp. 262-271 (13 pages).

Non-Final Office Action, U.S. Appl. No. 12/466,044, dated May 7, 2012, 35 pages.

Non-Final Office Action, U.S. Appl. No. 12/628,131, dated May 11, 2012, 35 pages.

Parodi, J.C. et al., "Transfemoral Intraluminal Graft Implantation for Abdominal Aortic Aneurysms", Ann Vasc Surg.; Nov. 1991; vol. 5, Issue 6, pp. 491-499 (9 pages).

Powell, J.T. et al.; "*Final 12-year Follow-up of Surgery* Versus *Surveillance in the UK Small Aneurysm* Trial"; Br. J. Surg.; Jun. 2007; vol. 94, Issue 6, pp. 702-708 (7 pages).

Volodos, N.L. et al.; "Clinical Experience of the use of Self-Fixing Synthetic Prostheses for Remote Endoprosthetics of the Thoracic and the Abdominal Aorta and Iliac Arteries Through the Femoral Artery and as Intraoperative Endoprosthesis for Aorta Reconstruction"; Kharkov Research Institute of General and urgent Surgery; J. Vasa Diseases-Suppl.; 1991; vol. 33, pp. 93-95 (5 pages).

Zarins, C.K.; "AneuRx Stent Graft Versus Open Surgical Repair of Abdominal Aortic Aneurysms: Multicenter Prospective Clinical Trial"; J Vasc Surg; Feb. 1999; vol. 29, Issue 2, pp. 292-308 (19 pages).

Zarins C.K.; "Endovascular Repair or Surveillance of Patients with Small AAA"; Eur. J. Vasc. Endovasc. Surg.; May 2005; vol. 29, Issue 5; pp. 496-503; located at www.sciencedirect.com (9 pages).

Kahraman, H. et al., "The Diameters of the Aorta and Its Major Branches in Patients with Isolated Coronary Artery Ectasia," Texas Heart Institute Journal; 2006, vol. 33, No. 4, pp. 463-468.

Non-Final Office Action, U.S. Appl. No. 12/958,381, dated Aug. 9, 2012, 30 pages.

Final Office Action; U.S. Appl. No. 12/466,044; dated Sep. 14, 2012; 9 pages.

Final Office Action; U.S. Appl. No. 12/628,131; dated Nov. 21, 2012; 19 pages.

Final Office Action; U.S. Appl. No. 12/958,383; dated Jan. 9, 2013; 29 pages.

Final Office Action; U.S. Appl. No. 12/958,381; dated Jan. 31, 2013; 36 pages.

International Search Report and Written Opinion, PCT/US2010/035003, Mailed on Feb. 9, 2011, Applicant: Altura Medical, Inc., 10 pages.

Non-Final Office Action, U.S. Appl. No. 12/958,374, dated Aug. 16, 2012, 28 pages.

Non-Final Office Action, U.S. Appl. No. 12/958,378, dated Aug. 16, 2012, 25 pages.

Non-Final Office Action, U.S. Appl. No. 12/958,383, dated Aug. 16, 2012, 28 pages.

Non-Final Office Action, U.S. Appl. No. 12/466,044, dated Jan. 3, 2013, 12 pages.

Australian Patent Examination Report No. 1, Australian Patent Application No. 2012203709; dated Jan. 30, 2013; 4 pages.

Australian Patent Examination Report No. 1, Australian Patent Application No. 2012203705; dated Jan. 31, 2013; 4 pages.

Australian Patent Examination Report No. 1, Australian Patent Application No. 2012203708; dated Feb. 1, 2013; 5 pages.

Japanese Office Action, Japanese Application No. 2012-511058, mailed on Apr. 3, 2014, 38 pages.

Final Office Action, U.S. Appl. No. 12/466,044, mailed on Jun. 19, 2014, 15 pages.

Chinese Office Action, Chinese Application No. 2009801268217, mailed May 7, 2014, 12 pages.

Japanese Office Action; Japanese Patent Application No. 2011-509771, mailed May 28, 2014, 10 pages.

Non-Final Office Action; U.S. Appl. No. 12/958,383, mailed on Jul. 31, 2014, 45 pages.

International Search Report and Written Opinion; App. No. PCT/US2013/054438, mailed on Feb. 7, 2014, Applicant: Andrew H. Cragg, 23 pages.

Dereume, J.P. et al., "Edoluminal Treatment of Abdominal Aortic Aneurysm with the Corvita Endovascular Graft. Results of a Single-Center, Prospective Feasibility Study of 90 Patients," Journal of Endovascular Surgery; Nov. 1996, vol. 3. 1 page.

Sanchez, Luis et al., "Early Experience with the Corvita Endoluminal Graft for Treatment of Arterial Injuries," From the Divisions of Vascular Surgery and Interventional Radiology, Montefiore Medical Center, New York. Presented May 31, 1997. 7 pages.

Sitsen, M. et al., "Deformation of Self-Expanding Stent-Grafts Complicating Edovascular Peripheral Aneurysm Repair," J Endovascular Surgery, 1999. 5 pages.

U.S. Appl. No. 13/963,912, filed Aug. 9, 2013, Cragg et al.

U.S. Appl. No. 13/964,013, filed Aug. 9, 2013, Cragg et al.

Chinese Preliminary Examination Report; Chinese Patent Application No. 100876, mailed on Mar. 30, 2012, 1 page.

Australian Patent Examination Report No. 1; Australian Patent Application No. 2012203707, mailed on Jan. 31, 2013, 4 pages.

Non-Final Office Action; U.S. Appl. No. 13/237,822, mailed on Dec. 5, 2013, 11 pages.

Final Office Action, U.S. Appl. No. 12/628,131, mailed on Oct. 8, 2014, 20 pages.

Non-Final Office Action; U.S. Appl. No. 12/956,381, mailed on Oct. 3, 2014, 17 pages.

Chinese Office Action; Chinese Application No. 200980126821.7, mailed Sep. 11, 2014, 5 pages.

Chinese Office Action, Chinese Application No. 201080062913.6, mailed on Nov. 15, 2014, 13 pages.

Japanese Office Action, Japanese Application No. 2012-542171, mailed on Sep. 24, 2014, 2 pages.

\* cited by examiner

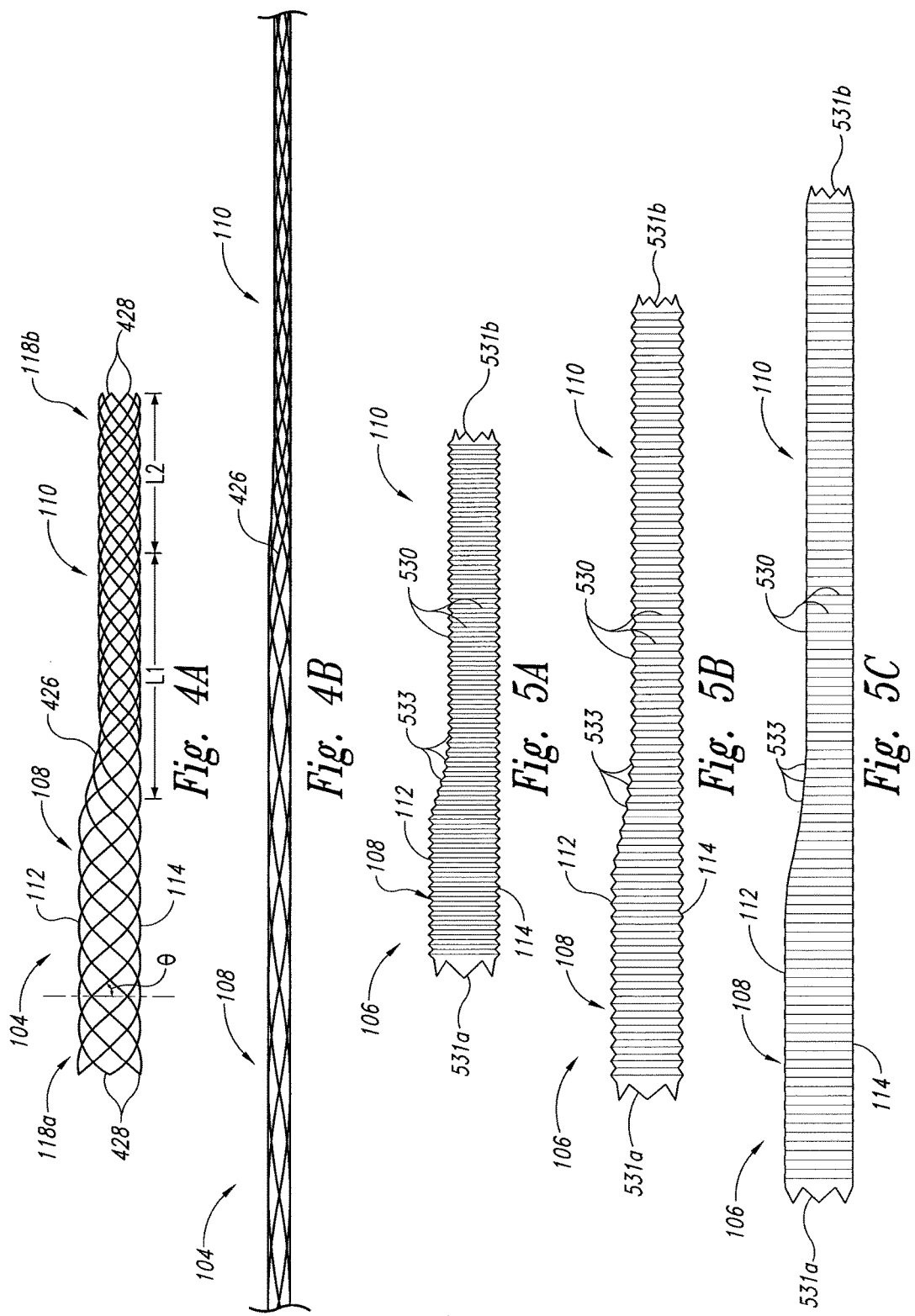

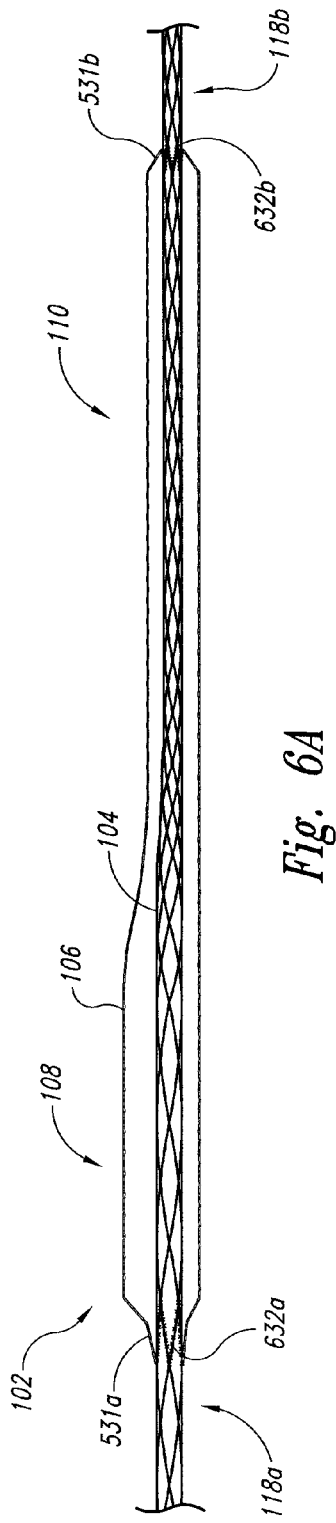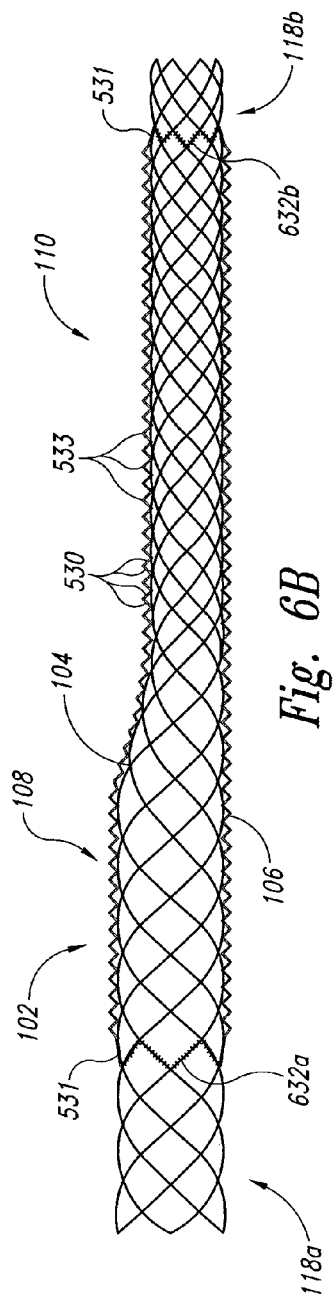

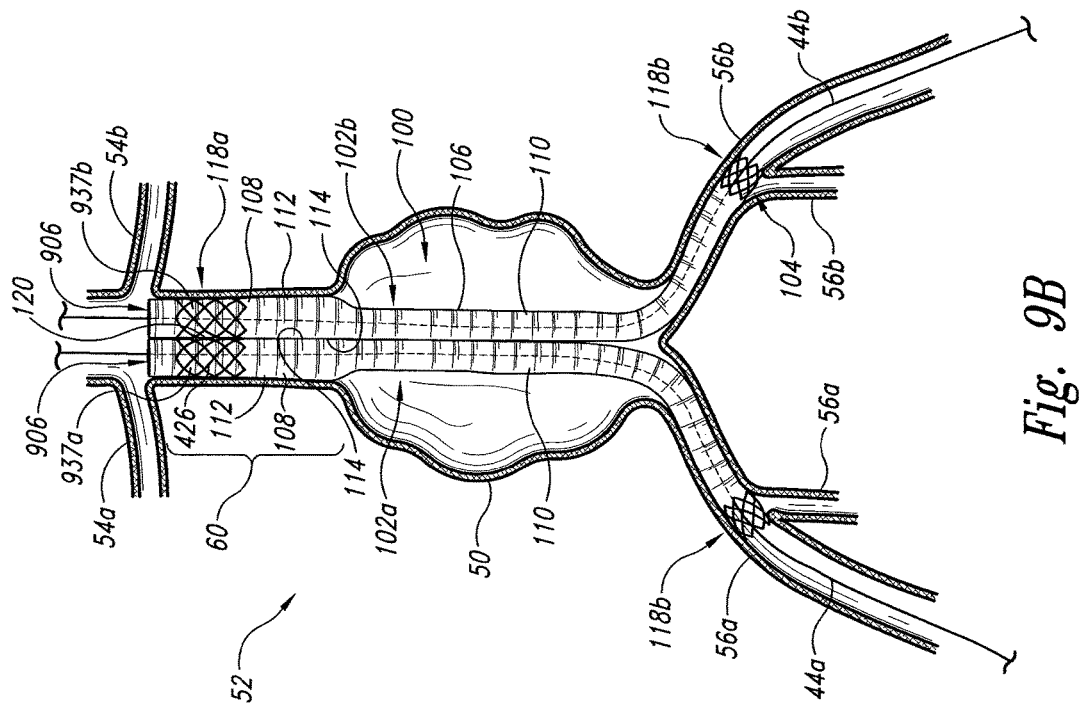
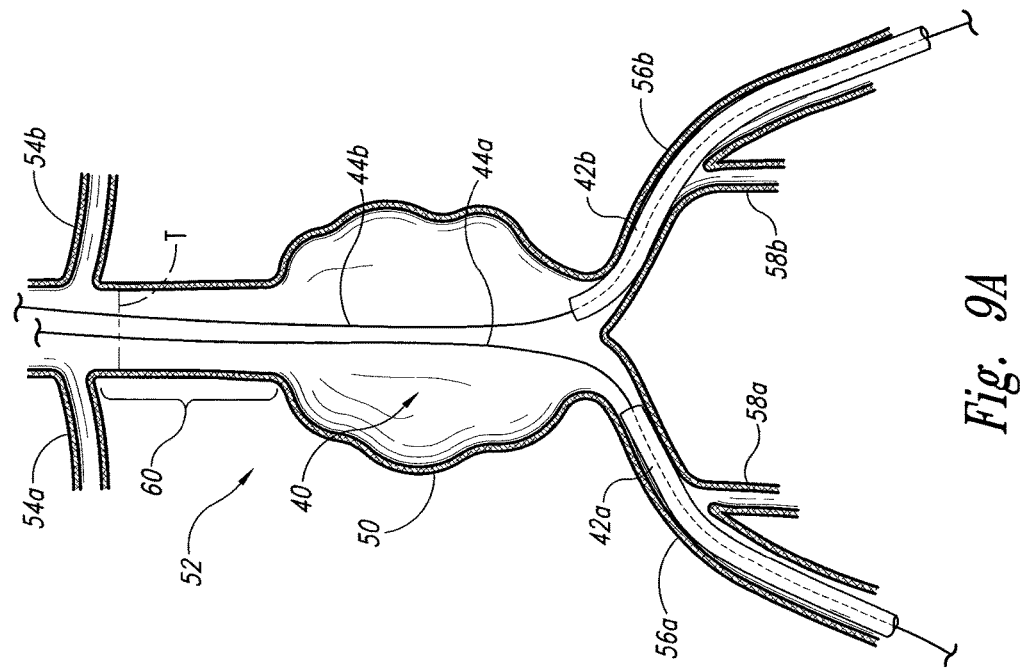

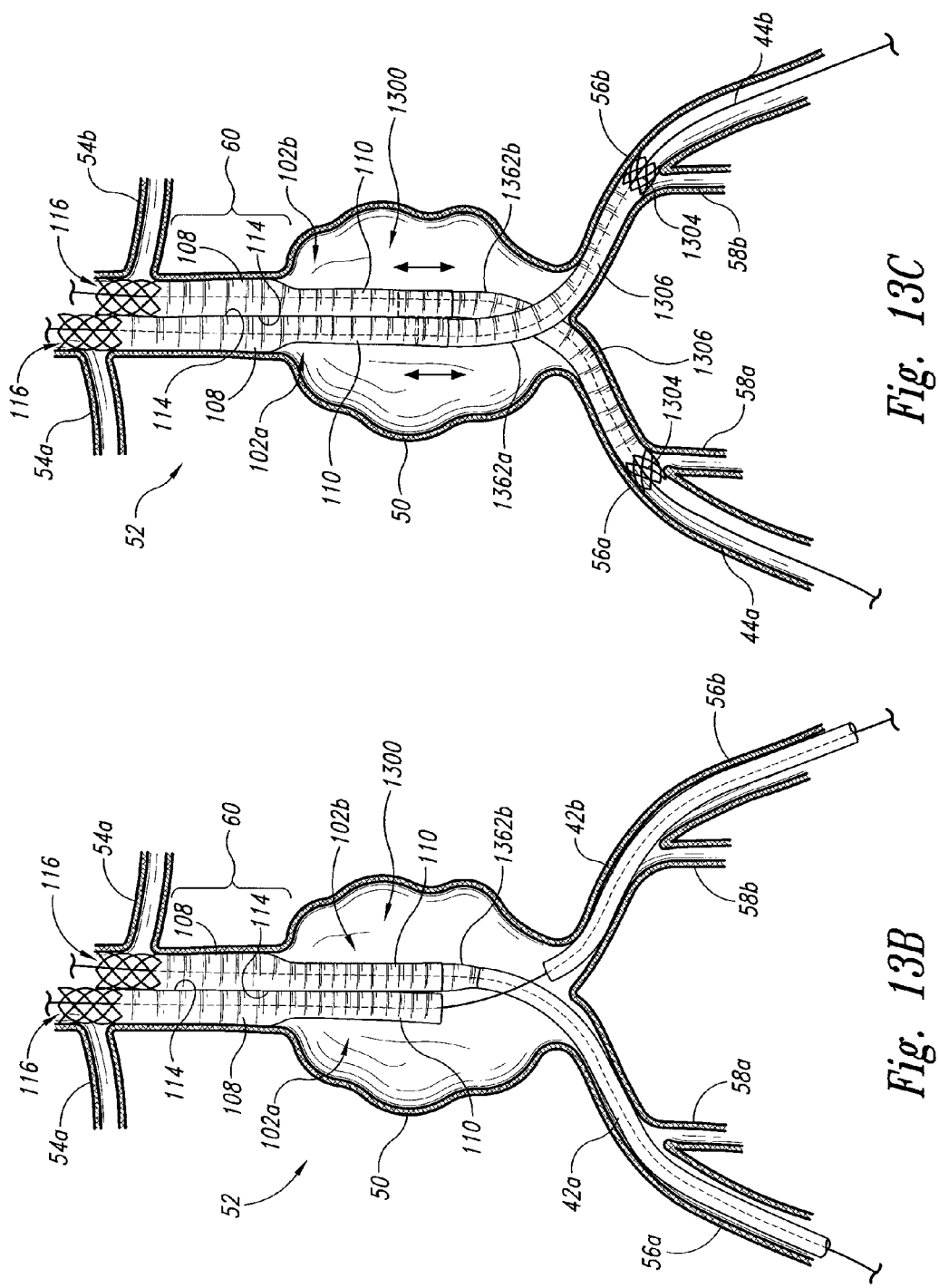

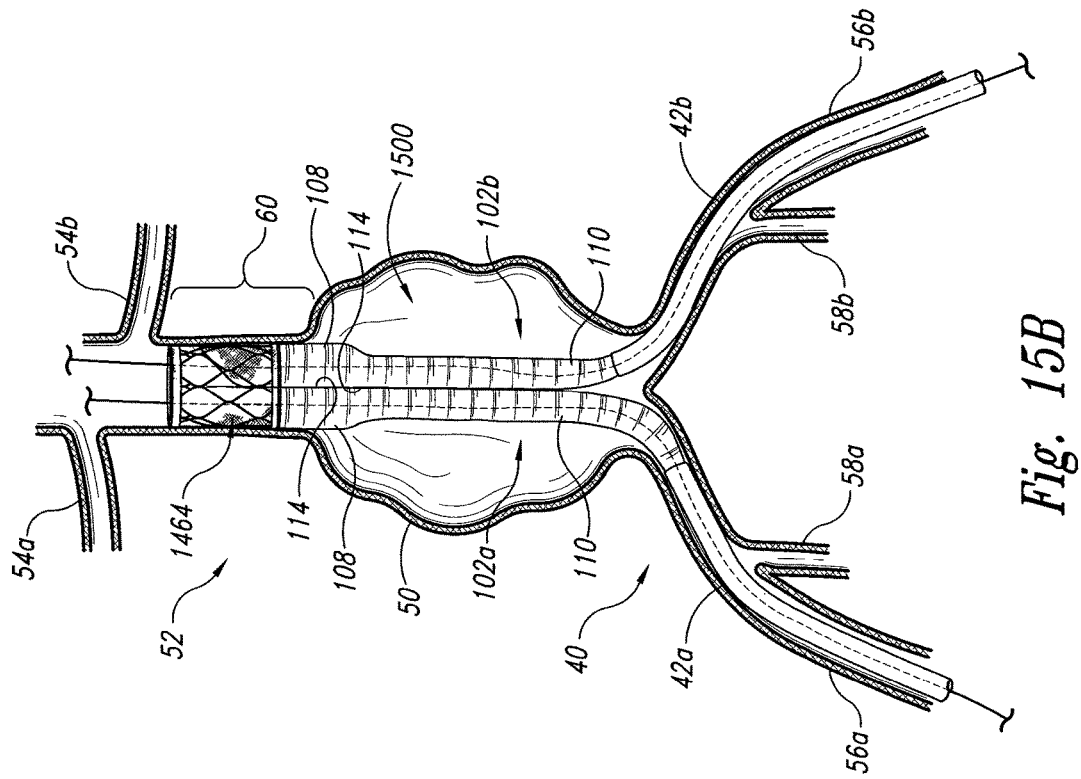
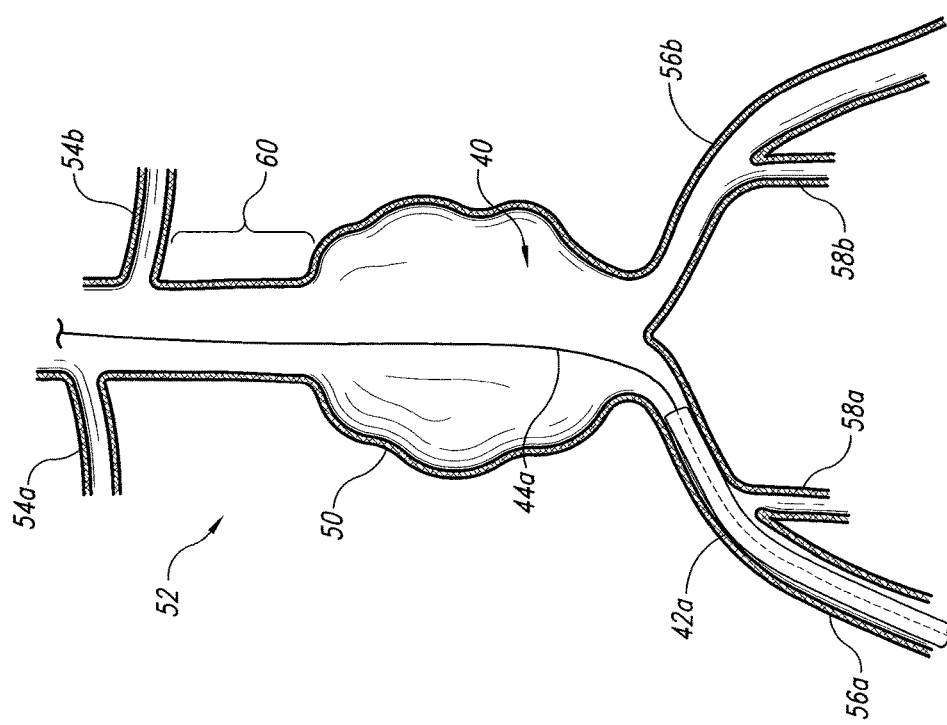

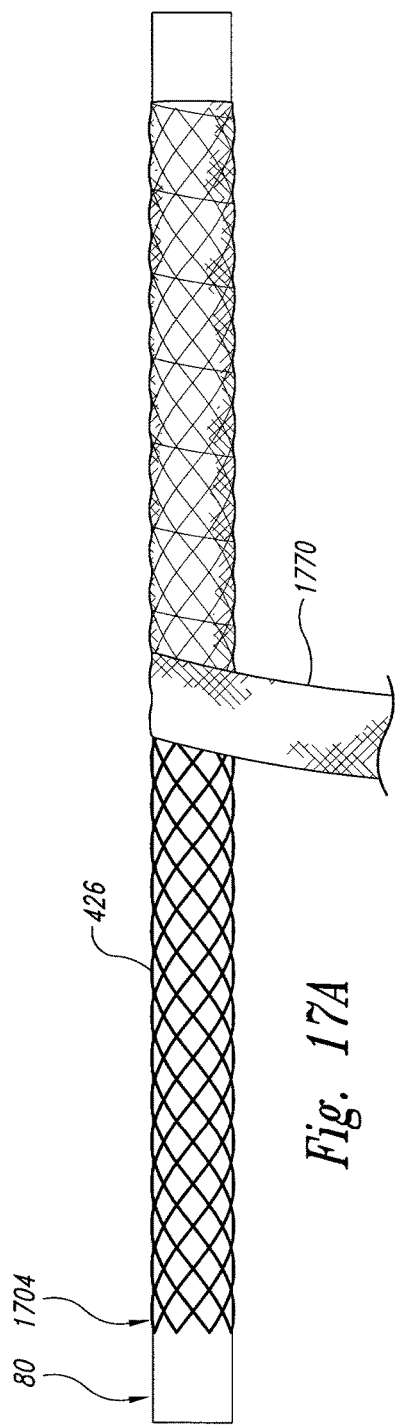
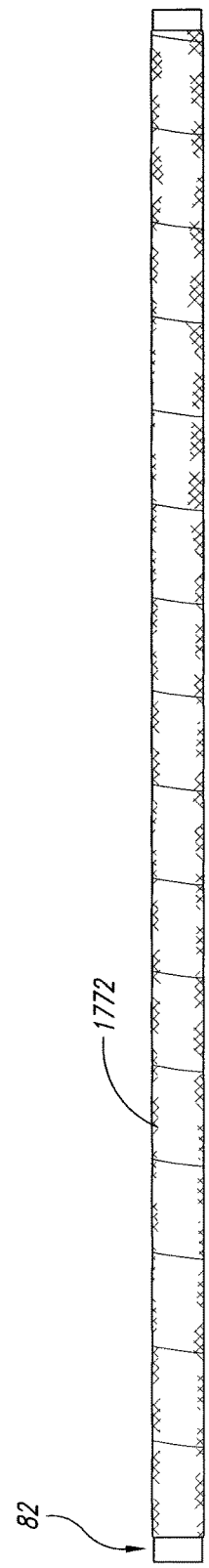
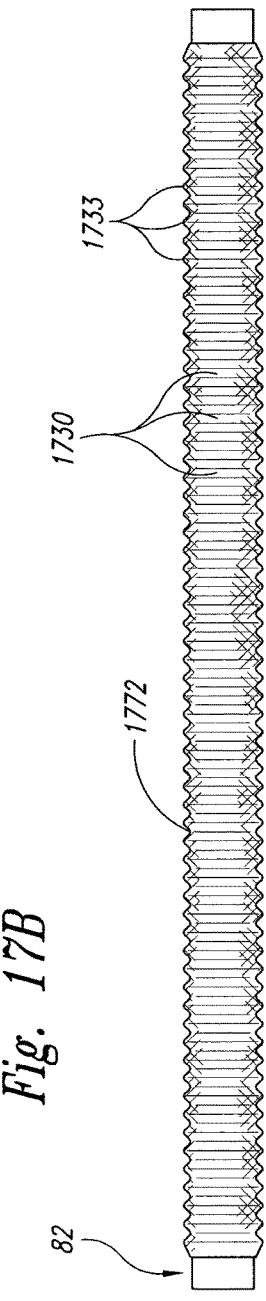
Fig. 17A
Fig. 17B
Fig. 17C

MODULAR ENDOGRAFT DEVICES AND ASSOCIATED SYSTEMS AND METHODS

CROSS-REFERENCE TO RELATED APPLICATIONS

The present application claims priority to each of the following U.S. Provisional Applications:

(A) U.S. Provisional Application No. 61/265,713, filed on Dec. 1, 2009, entitled "IMPROVED SYSTEMS AND METHODS FOR MODULAR ABDOMINAL AORTIC ANEURYSM GRAFT".

(B) U.S. Provisional Application No. 61/293,581, filed Jan. 8, 2010, entitled "IMPROVED SYSTEMS AND METHODS FOR MODULAR ABDOMINAL AORTIC ANEURYSM GRAFT".

(C) U.S. Provisional Application No. 61/311,735, filed Mar. 8, 2010, entitled "ENHANCED SYSTEMS AND METHODS FOR MODULAR ABDOMINAL AORTIC ANEURYSM GRAFT"; and (D) U.S. Provisional Application No. 61/320,646, filed Apr. 2, 2010, entitled "SYSTEMS AND METHODS FOR A MODULAR ABDOMINAL AORTIC ANEURYSM GRAFTING AND DEVICES FOR THE SAME".

All of the foregoing applications are incorporated herein by reference in their entireties.

TECHNICAL FIELD

The present technology generally relates to endograft devices and methods for percutaneous endovascular delivery of the endograft devices across aneurysms. In particular, several embodiments are directed toward a modular bi-luminal endograft device with independently positioned components for endovascular aneurysm repair.

BACKGROUND

An aneurysm is a dilation of a blood vessel at least 1.5 times above its normal diameter. The dilated vessel can form a bulge known as an aneurysmal sac that can weaken vessel walls and eventually rupture. Aneurysms are most common in the arteries at the base of the brain (i.e., the Circle of Willis) and in the largest artery in the human body, the aorta. The abdominal aorta, spanning from the diaphragm to the aortoiliac bifurcation, is the most common site for aortic aneurysms. The frequency of abdominal aortic aneurysms ("AAAs") results at least in part from decreased levels of elastins in the arterial walls of the abdominal aorta and increased pressure due to limited transverse blood flow.

Aneurysms are often repaired using open surgical procedures. Surgical methods for repairing AAAs, for example, require opening the abdominal region from the breast bone to the pelvic bone, clamping the aorta to control bleeding, dissecting the aorta to remove the aneurysmal section, and attaching a prosthetic graft to replace the diseased artery. The risks related to general anesthesia, bleeding, and infection in these types of open surgical repairs result in a high possibility of operative mortality. Thus, surgical repair is not a viable option for many patients. Moreover, the recovery process is extensive for the patients fit for surgical repair. An open surgical repair of an AAA generally requires seven days of post-operational hospitalization and, for uncomplicated operations, at least six to eight weeks of recovery time. Thus, it is a highly invasive and expensive procedure.

Minimally invasive surgical techniques that implant prosthetic grafts across aneurysmal regions of the aorta have been developed as an alternative or improvement to open surgery. Endovascular aortic repairs ("EVAR"), for example, generally require accessing an artery (e.g., the femoral artery) percutaneously or through surgical cut down, introducing guidewires into the artery, loading an endograft device into a catheter, and inserting the loaded catheter in the artery. With the aid of imaging systems (e.g., X-rays), the endograft device can be guided through the arteries and deployed from a distal opening of the catheter at a position superior to the aneurysm. From there, the endograft device can be deployed across the aneurysm such that blood flows through the endograft device and bypasses the aneurysm.

EVAR devices should be implanted at a precise location across the aneurysmal region and securely fixed to the vessel wall because improper placement, migration, and/or projection of the endograft device into branching vessels may interfere with the blood flow to nearby physiological structures. For example, to avoid impairing renal functions, the endograft device should not inhibit blood flow to the renal arteries. In addition to the variations in the vasculature between patients, the characteristics of the aneurysms themselves can also pose challenges because of the anatomical variations and the different structural features of individual aneurysms. For example, the vascular bifurcation at the iliac arteries and the angulation of aneurysmal sacs are both known to pose challenges to methods and devices for treating AAAs. Conventional systems address these challenges by having many different EVAR devices with different sizes and shapes.

BRIEF DESCRIPTION OF THE DRAWINGS

FIGS. 4A and 4B are side views of an integrated frame in an expanded configuration and in a low-profile configuration, respectively, in accordance with an embodiment of the technology.

FIGS. 5A-C are side views of a cover being extended from an expanded configuration to a low-profile configuration in accordance with an embodiment of the technology.

FIGS. 6A and 6B are cross-sectional views of an endograft device in a low-profile configuration and in an expanded configuration, respectively, in accordance with embodiments of the technology.

FIGS. 9A and 9B are schematic views of a two-part modular endograft system being deployed across an aneurysm in accordance with an embodiment of the technology.

FIGS. 13A-C are schematic views of a four-part modular endograft system being deployed across an aneurysm in accordance with an embodiment of the technology.

FIGS. 15A and 15B are schematic views of a three-part modular endograft system being deployed across an aneurysm in accordance with an embodiment of the technology.

FIGS. 17A-E are views of coating layers being applied to an integrated frame in accordance with an embodiment of the technology.

DETAILED DESCRIPTION

Specific details of several embodiments of the technology are described below with reference to FIGS. 1A-17E. Although many of the embodiments are described below with respect to devices that at least partially repair abdominal aortic aneurysms ("AAAs"), other applications and other embodiments are within the scope of the technology. For example, the technology can be used to repair aneurysms in other portions of the vasculature. Additionally, several other embodiments of the technology can have different configurations, components, or procedures than those described in this section. A person of ordinary skill in the art, therefore, will accordingly understand that the technology may have other embodiments with additional elements, or the technology may have other embodiments without several of the features shown and described below with reference to FIGS. 1A-17E.

With regard the use of "superior" and "inferior" within this application, inferior generally refers being situated below or directed downward, and superior generally refers to being situated above or directed upward.

With regard to the use of "expansion" and "constriction" within this application, expansion refers to a radial increase in a cross-sectional dimension of a device or component, and constriction refers to a radial decrease in the cross-sectional dimension of the device or component. For example, FIG. 4A shows an integrated frame 104 in an expanded configuration, and FIG. 4B shows the integrated frame 104 in a constricted configuration.

With regard to the use of "contraction" and "extension" within this application, contraction refers to a longitudinal decrease in the length of a device or component, and extension refers to a longitudinal increase in the length of the device or component. For example, FIG. 5A shows a cover 106 in a contracted configuration, and FIG. 5C shows the cover 106 in an extended configuration.

With regard to the terms "distal" and "proximal" within this application, the terms can reference a relative position of the portions of an implantable device and/or a delivery device with reference to an operator. Proximal refers to a position closer to the operator of the device, and distal refers to a position that is more distant from the operator of the device.

1. Endograft System Structures
1.1 Selected Endograft Devices

Figure 1A:
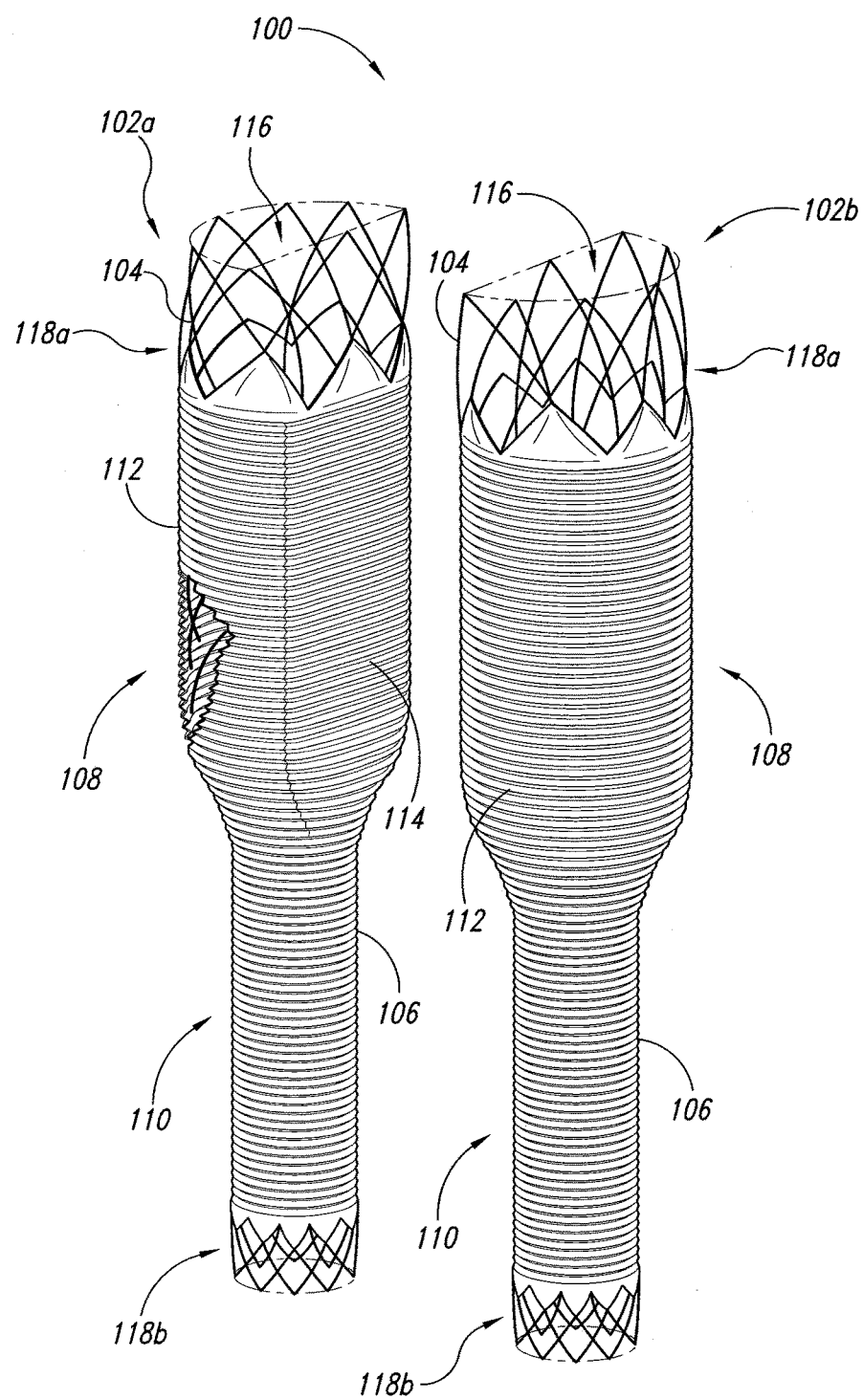
FIG. 1A is a partial cut-away, isometric view of a modular endograft system configured in accordance with an embodiment of the technology.
Figure 1B:
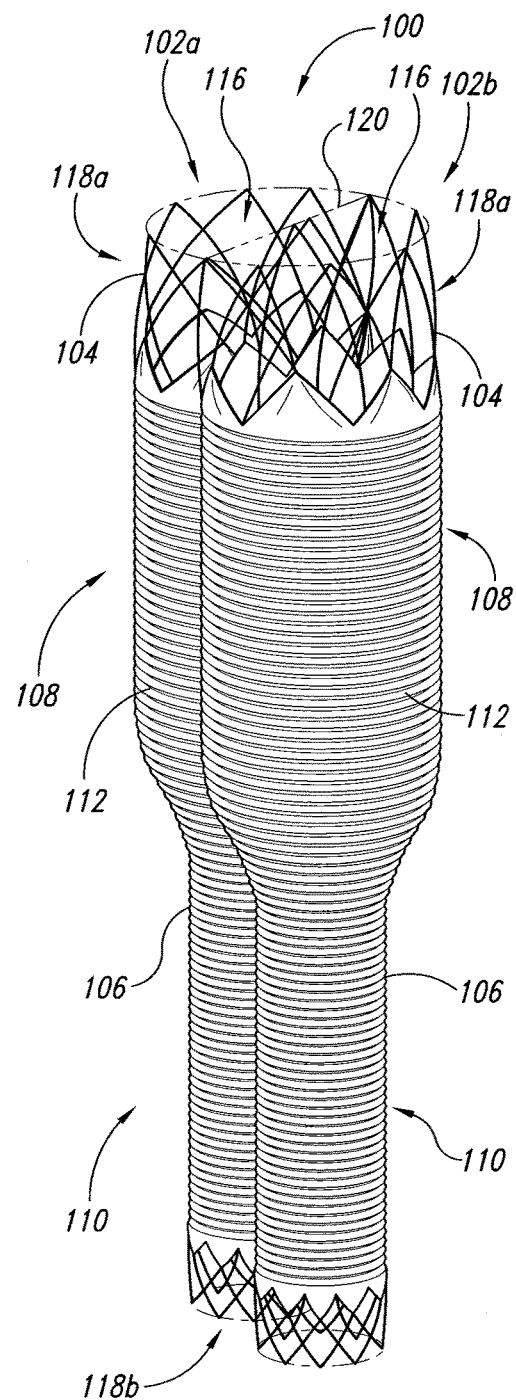
FIG. 1B is an isometric view of the modular endograft system of FIG. 1A configured in accordance with an embodiment of the technology.

FIGS. 1A and 1B are isometric views of a-modular endograft system 100 ("system 100") in accordance with an embodiment of the technology. The system 100 can include separate endograft devices 102 (identified individually as a first endograft device 102a and a second endograft device 102b) that can be coupled, mated, or otherwise substantially sealed together in situ. Each endograft device 102, for example, can include an integrated frame 104 ("frame 104") and a substantially impermeable cover 106 ("cover 106") extending over at least a portion of the frame 104. The frame 104 and the cover 106 of an individual endograft device 102 can form a discrete lumen 116 through which blood can flow to bypass an aneurysm. In operation, the endograft devices 102 are generally delivered separately and positioned independently across the aneurysm.

As shown in FIGS. 1A and 1B, each endograft device 102 includes a superior portion 108 and an inferior portion 110. The superior portion 108 can include a convexly curved outer wall 112 and a septal wall 114. As shown in FIG. 1A, the septal wall 114 can be substantially flat such that the superior portion 108 forms a "D" shape at a superior portion of the lumen 116. In other embodiments, the septal wall 114 can be convexly curved with a larger radius of curvature than the outer wall 112 such that the superior portion 108 forms a complex ellipsoid having another D-shaped cross-section at the superior portion of the lumen 116. In further embodiments, the superior portion 108 can have asymmetrical shapes or other suitable cross-sectional configurations that can mate with each other in the septal region and mate with an arterial wall around the periphery of the outer wall 112. The inferior portion 110 can have a circular cross-sectional shape as illustrated in FIG. 1A, or the inferior portion 110 can have an elliptical shape, a rectangular shape, an asymmetrical shape, and/or another suitable cross-sectional shape for an inferior portion of the lumen 116.

The superior portions 108 of the endograft devices 102 are mated together and at least substantially sealed along the septal walls 114 within the aorta above the aneurysm. In some embodiments, the superior portion 108 can be approximately 2-4 cm in length to adequately fix the outer walls 112 to the arterial walls such that they are at least substantially sealed together. In other embodiments, the superior portion 108 can be longer or shorter. In one embodiment in accordance with the technology, the inferior portions 110 can extend through an inferior portion of the aneurysm and into corresponding iliac arteries to bypass the aneurysm. In another embodiment, one or both inferior portions 110 can terminate within the aneurysm to form what is known to those skilled in the art as a "gate." As described in further detail below, limbs (not shown) can be attached to the proximal ends of the inferior portions 110 and extended into the iliac arteries to bypass the aneurysm.

In the embodiment shown in FIGS. 1A and 1B, the frames 104 have bare end portions 118 (identified individually as first end portions 118a and second end portions 118b) that extend beyond the covers 106. As shown in FIGS. 1A and 1B, the first end portion 118a can extend distally from the superior terminus of the cover 106, and the second end portion 118b can extend proximally from the inferior terminus of the cover 106. In some embodiments, the end portions 118 can be trumpeted or flared to interface with the arterial walls of the aorta and/or the iliac arteries. This can promote cell ingrowth that strengthens the seal between the endograft devices 102 and the adjacent arteries.

The end portions 118 can also increase the available structure for securing the endograft device 102 to the artery and increase the surface area of the covers 106 for sealably fixing the endograft devices 102 to arterial walls. This decreases the precision necessary to position the endograft devices 102 and increases the reliability of the implanted system 100. For example, a short infrarenal aortic neck (e.g., less than 2 cm) generally requires precise placement of the endograft devices 102 to preserve blood flow to the renal arteries while still providing enough surface area for the endograft devices 102 to be properly affixed with the aorta. In the embodiment shown in FIGS. 1A and 1B, however, the first end portions 118a can be placed at the entrance of the renal arteries to allow lateral blood flow into the renal arteries and provide a larger structure for fixing the endograft devices 102 to the arterial wall and a larger sealing area with the arterial wall. The end portions 118 can also provide accessible sites for recapture (e.g., by guidewires, bead and collet, etc.) that enhance the accuracy of positioning the endograft devices 102 across the aneurysm.

During deployment of the system 100, each endograft device 102 can be delivered independently to an aneurysmal region in a low-profile configuration. The low-profile configuration has a first cross-sectional dimension and a first length that can facilitate percutaneous endovascular delivery of the system 100. Because each device 102 extends around only a portion of the vessel periphery, the individual endograft devices 102 can be constricted (i.e., radially collapsed) to a smaller diameter than conventional AAA devices with a single superior portion that extends around the complete periphery of the vessel wall. In some embodiments, for example, each of the endograft devices 102 can have a diameter of 25 mm in the expanded configuration, and can be constricted to a diameter of 4 mm in the low-profile configuration to be percutaneously deployed across the aneurysm through a 12 F catheter. Additionally, as described in more detail below, because each endograft device 102 is delivered independently, the end portions 118 and fenestrations can facilitate staggering the endograft devices 102 to accommodate asymmetrical anatomies.

At a target site in the aneurysmal region, the endograft devices 102 can self-expand to an expanded configuration (e.g., shown in FIGS. 1A and 1B). The expanded configuration can have a second cross-sectional dimension greater than the first cross-sectional dimension and a second length less than the first length. In the expanded configuration shown in FIG. 1B, the septal wall 114 (FIG. 1A) of the first endograft device 102a can be forced against the opposing septal wall 114 of the second endograft device 102b. When in situ within the aorta, the forces between the opposing septal walls 114 form a septum 120 in which the first and second septal walls 114 are at least substantially sealed together to prevent blood from flowing between the endograft devices 102 and into the aneurysm. Additionally, as shown in FIG. 1B, the texture (e.g., ribbing) on the covers 106 can mate at the septum 120 to further strengthen the seal between the septal walls 114. Similarly, the texture of the cover 106 on the outer walls 112 can interface with the adjacent vessel walls to strengthen the seal around the periphery of the endograft devices 102.

In operation, the system 100 can prevent blood from collecting in a diseased aneurysmal portion of a blood vessel (e.g., the aorta, the iliac arteries, etc.). Rather, the system 100 can direct blood into the lumens 116, funnel the blood through the superior and inferior portions 108 and 110, and discharge the blood into healthy portions of the iliac arteries, thereby at least substantially bypassing the aneurysm. The bifurcated system 100 facilitates independent positioning of the first and second endograft devices 102 to accommodate disparate structures and morphologies of the abdominal aorta and/or iliac arteries. For example, the first endograft device 102a can be positioned independently in a desired location without being constrained by a desired placement of the second endograft device 102b. Accordingly, the system 100 can easily adapt to a variety of different anatomies and thereby provide a modular alternative to customized endograft systems.

1.2 Select Embodiments of Superior Portions

Figure 2A:
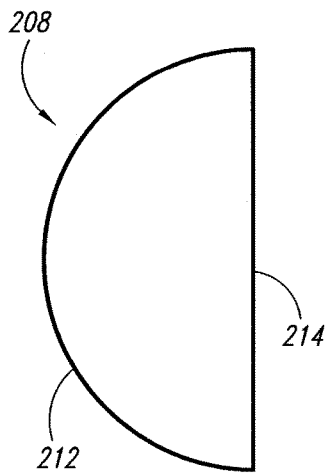
FIGS. 2A-C are cross-sectional top views of superior portions for endograft devices shaped in accordance with embodiments of the technology.
Figure 2B:
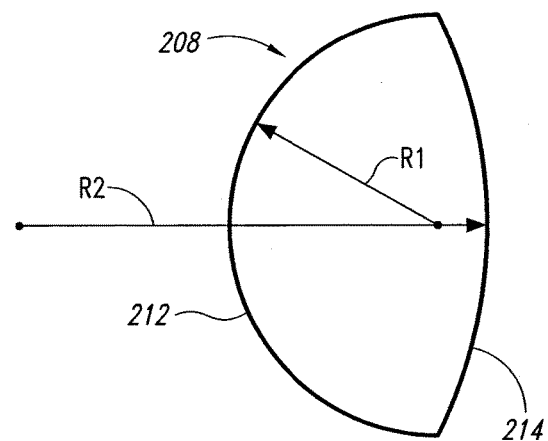
Figure 2C:
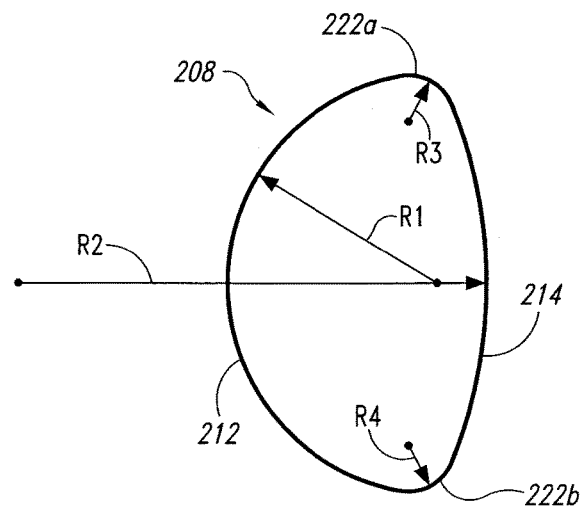

FIGS. 2A-C are cross-sectional top views of superior portions 208 of endograft devices (e.g., endograft devices 102 shown in FIGS. 1A and 1B) shaped in accordance with embodiments of the technology. The superior portions 208 can have generally similar features as the superior portions 108 shown in FIGS. 1A and 1B. For example, each superior portion 208 includes an outer wall 212 and a septal wall 214. The outer wall 212 is generally semi-circular, but can otherwise be configured according to the shape, geometry, and/or morphology of an arterial wall. The septal wall 214 can be shaped to mate with a complementary septal wall 214 of another endograft device. More specifically, in the embodiment illustrated in FIG. 2A, the superior portion 208 includes a convexly curved, substantially semi-circular outer wall 212 and a substantially flat septal wall 214. Thus, the superior portion 208 forms a "D" shape and can be part of a system (e.g., the system 100 shown in FIGS. 1A and 1B) including a corresponding D-shaped superior portion of a mating endograft device.

In other embodiments, both the outer wall 212 and the septal wall 214 can be convexly curved such that the superior portion 208 forms a complex ellipsoid with at least two distinct radii. FIG. 2B, for example, shows the superior portion 208 can include a convexly curved outer wall 212 that has a first radius R1 and a convexly curved septal wall 214 that has a second radius R2 greater than the first radius R1. In the embodiment illustrated in FIG. 2B, the second radius R2 is substantially greater than the first radius R1 such that the superior portion 208 has a substantially D-like shape.

Similarly, the superior portion 208 shown in FIG. 2C includes the convexly curved outer wall 212 that has the first radius of curvature R1 and the convexly curved septal wall 214 that has the second radius of curvature R2 greater than the first radius R1. As shown in FIG. 2C, the superior portion 208 can further include convexly curved corner sections 222 (identified individually as a first corner section 222a and a second corner section 222b). The first corner section 222a can have a third radius R3, and the second corner section 222b can have a fourth radius R4 distinct from or equivalent to the third radius R3. In the embodiment shown in FIG. 2C, the third and fourth radii R3 and R4 are substantially smaller than the first and second radii R1 and R2 such that the superior portion 208 forms another substantially D-like shape. In other embodiments, the superior portion 208 can include greater or smaller radii, more or less curved portions, and/or can have another shape suitable for mating and at least substantially sealing two endograft devices together within a blood vessel.

Figure 2E:
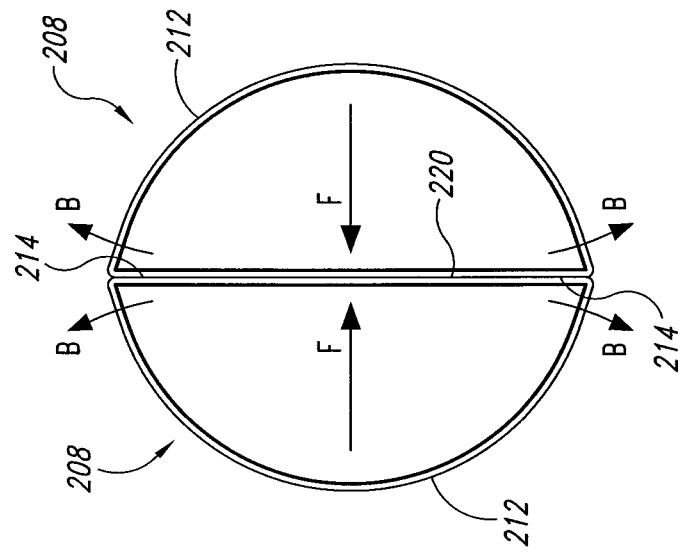
FIGS. 2D and 2E are cross-sectional top views of the superior portion of FIG. 2B being mated with a complementary superior portion in accordance with an embodiment of the technology.
Figure 2D:
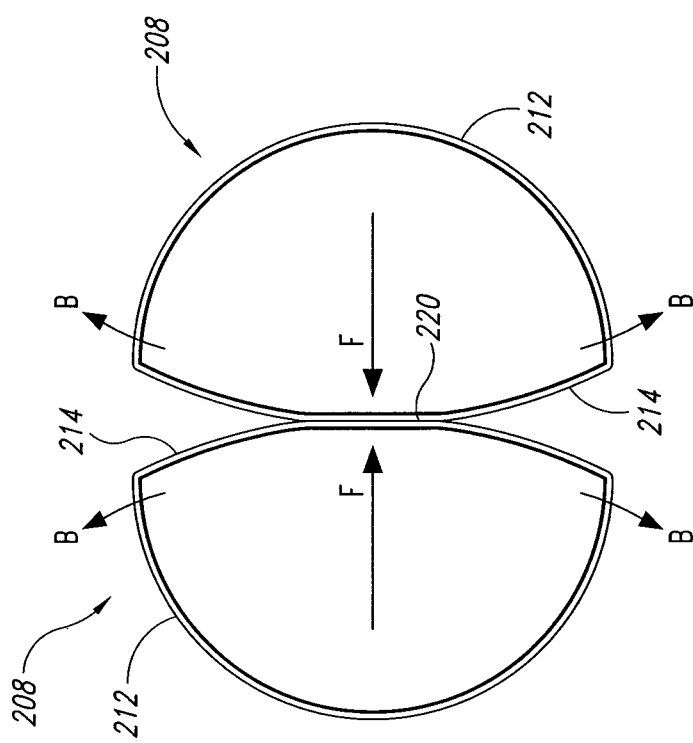

FIGS. 2D and 2E are cross-sectional top views of the superior portion 208 of FIG. 2B being mated with a complementary superior portion 208 to form a sealed septum 220 in accordance with an embodiment of the technology. More specifically, FIG. 2D shows the superior portions 208 being pressed toward one another by a force F. The force F can derive from the self-expansion of the superior portions 208 within the confined space of an aorta. As shown in FIG. 2D, the force F can cause the superior portions 208 to contact one another near the center of their respective convexly curved septal walls 214 and flatten the septal walls 214. The apposition of the septal walls 214 can generate an outward force generally tangential to the septal walls 214 that can cause a slight outward bowing B near the interface of the outer and septal walls 212 and 214.

As shown in FIG. 2E, the force F can continue to press the superior portions 208 against one another until the convexly curved septal walls 214 straighten to form the septum 220. The initial convexities of the septal walls 214 can induce more pressure between the septal walls 214 than straight septal walls (e.g., FIG. 2A) and promote an even distribution of the force along the septum 220 to enhance the seal. Additionally, the outward bowing B can enhance the seal at the edges of the septal walls 214. The superior portions 208 shown in FIGS. 2A and 2C can be similarly joined to form the substantially straight septum 220. For example, the superior portion 208 shown in FIG. 2C can be pressed against a corresponding superior portion such that the relative forces between the superior portions 208 substantially straighten the septal walls 214 and corner sections 222 (e.g., approximately 60° to 90° between the outer and septal walls 112 and 114) to form the septum 220. In operation, the septum 220 can be at least substantially sealed to prevent fluids (e.g., blood) from flowing between the superior portions 208.

1.3 Select Embodiments of Transition Portions

Figures 3A, 3B:
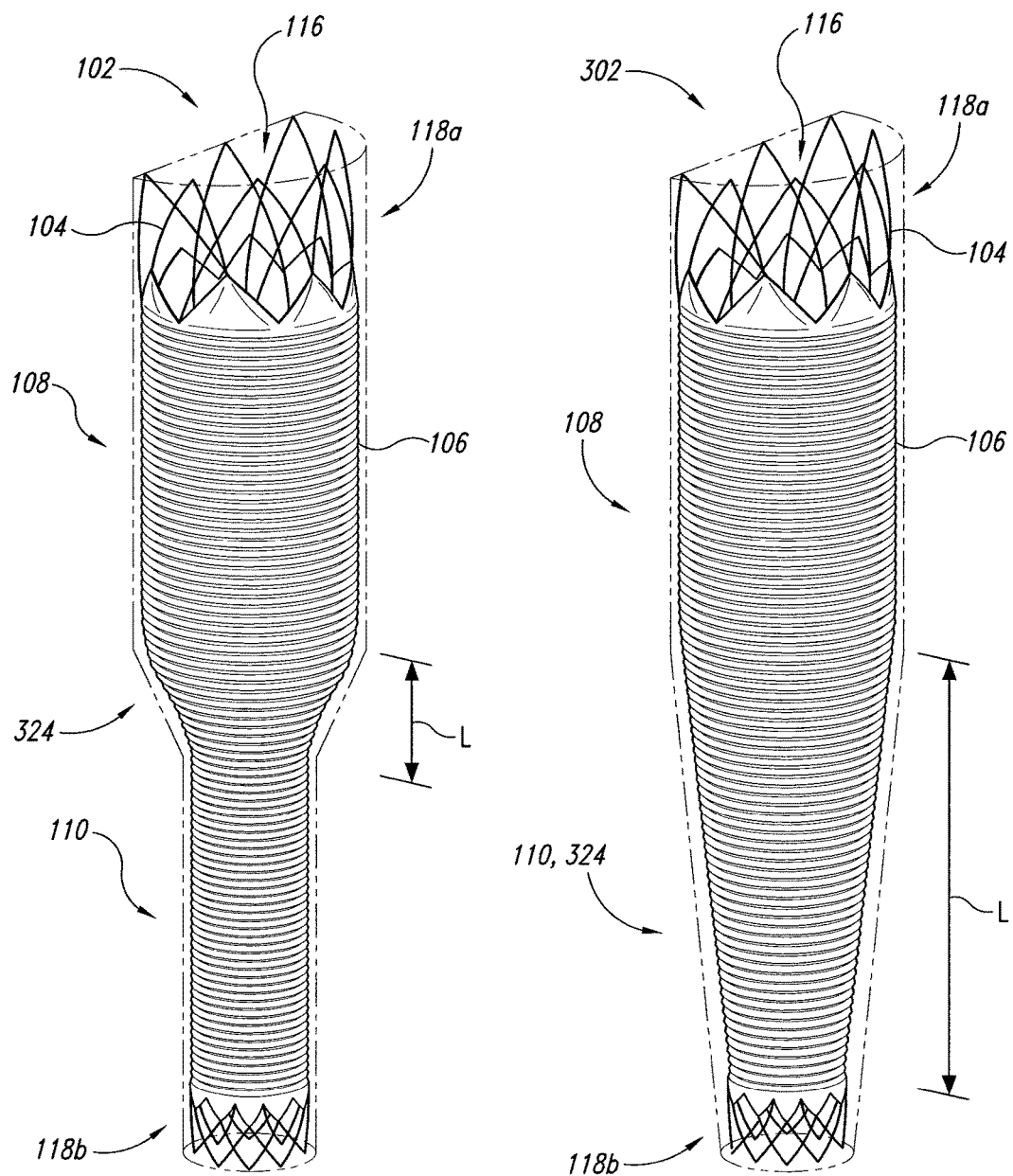
FIGS. 3A and 3B are isometric views of endograft devices configured in accordance with embodiments of the technology.

FIGS. 3A and 3B are isometric views of transition portions 324 of endograft devices configured in accordance with embodiments of the technology. The transition portions 324 can promote laminar blood flow by gradually changing the size of the lumen 116 from the wider, superior portion 108 to the narrower, inferior portion 110. Additionally, the transition portions 324 can be configured to reduce the downforce exerted on the endograft devices 102 as blood flows through the lumen 116.

More specifically, FIG. 3A is an isometric view of the endograft device 102 described above with reference to FIGS. 1A and 1B. The endograft device 102 includes the transition portion 324 positioned between the superior portion 108 and the inferior portion 110. As shown in FIG. 3A, the transition portion 324 can be tapered to gradually narrow the cross-section of the lumen 116 and thereby reduce disruptions to the blood flow. The transition portion 324 can have a length L related to the distance necessary to continue substantially laminar blood flow through the lumen 116. For example, in some embodiments, the length L can be 4 cm. In other embodiments, the length L can differ due to the geometry of the endograft device 102, the rheologic characteristics of the blood flow, and/or other relevant factors in decreasing turbulent blood flow. In other embodiments, the transition portion 324 can be sloped, stepped, and/or have another suitable shape that can decrease the cross-section of the lumen 116 from the superior portion 108 to the inferior portion 110 without inducing turbulent blood flow.

FIG. 3B is an isometric view of an endograft device 302 in accordance with another embodiment of the technology. The endograft device 302 can include generally similar features as the endograft 102 shown in FIG. 3A. However, the tapered transition portion 324 shown in FIG. 3B has a more gradual taper and a much greater length L than the transition portion 324 shown in FIG. 3A. As shown in FIG. 3B, the tapered transition portion 324 extends from the superior portion 108 to the second end portion 118b such that the transition portion 324 defines the inferior portion 110 (not visible). Accordingly, the tapered transition portion 324 can steadily degrease the cross-section of the lumen 116 to facilitate laminar blood flow through the lumen 116. The gradual taper of the transition portion 324 may, however, cause the endograft device 302 to migrate in the direction of blood flow more than the more aggressive taper of the transition portion 324 shown in FIG. 3A. Accordingly, the length L and angle of the tapered transition portion 324 can be optimized to mitigate migration of the endograft device 302 without inducing undo turbulent blood flow. In other embodiments, the transition portion 324 can optimize the geometry of a different shape (e.g., stepped) to maintain laminar blood flow and mitigate migration of the endograft device 302.

2. Endograft System Components 2.1 Integrated Frames

FIGS. 4A and 4B are side views of the integrated frame 104 described with reference to FIGS. 1A and 1B in an expanded configuration (FIG. 4A) and a low-profile configuration (FIG. 4B) in accordance with an embodiment of the technology. As discussed above, the frame 104 includes the superior portion 108, the inferior portion 110, and the exposed end portions 118. In some embodiments, the smallest radius of the outer wall 112 of each superior portion 108 in the expanded configuration may not be less than 10 mm (i.e., the smallest diameter of the superior portions 108 of mated endograft devices 102 is more than 20 mm).

As shown FIGS. 4A and 4B, the frame 104 can be a braided structure made from one or more continuous, interwoven wires 426 that provide a continuous, integrated support longitudinally along the length of the frame 104. For example, as shown in FIG. 4A, the wire 426 is braided such that a first longitudinal segment L1 of the frame 104 supports an adjacent second longitudinal segment L2 of the frame 104. Accordingly, each area of the frame 104 influences the radial expansion or contraction of an adjacent area of the frame. In some embodiments, the frame 104 is woven with one wire 426 that continuously crosses itself along the length of the frame 104. The intersections of the wire 426 may not be welded or otherwise fixed together such that they remain unbound to increase the flexibility of the frame 104. In other embodiments, the frame 104 includes a plurality of wires 426 that can be interwoven and/or concentrically layered to form the frame 104. The frame 104, for example, can include eight wires 426 in which several of the wires 426 can end at intermediate points along the length of the frame 104. Such a staggered, multi-wire construction prevents the wire ends from weakening the frame 104 and/or from wearing on a subsequently attached cover (e.g., the cover 106 shown in FIGS. 1A and 1B). The number of wires 426 can also vary at different sections along the length of the frame 104. For example, in one embodiment, the inferior portion 110 includes fewer wires 426 than the superior portion 108 such that the density or pitch of the wires 426 does not increase at inferior portion 110 and the frame 104. This enables the inferior portion 110 to have a small diameter in the constricted, low-profile configuration (FIG. 4B).

As shown in FIG. 4A, the wires 426 can form a loop 428 at one end portion 118 to reverse direction and continue weaving along the length of the frame 104 toward the opposite end portion 118. The optimal number of loops 428 at each end portion 118 can be associated with the diameter of the wires 426. Too few loops 428 can decrease the strength at the end portions 118 of the contracted frame 104 shown in FIG. 4A. Too many loops 428 can increase the profile of the extended frame 424 shown in FIG. 4B, and can also cause difficulty attaching the cover. A wire 426 with a diameter of 0.008 inch, for example, may have an optimal number of ten to twelve loops 428 (five to six at each end portion 118), whereas a wire 426 with a diameter of 0.009 inch may have an optimal number of twelve to fourteen loops 428. In other embodiments, the wires 426 can include more or less loops 428 to optimize characteristics of the frame 104. Additionally, the degree of curvature of each of the loops 428 can impact the durability of the wires 426. For example, tightly wound loops 428 with high degrees of curvature are subject to fatigue and failure at the end portions 118 because of the stress induced upon constriction. Therefore, in some embodiments, the degree of curvature of the loops 428 can be the least degree of curvature permissible for the optimal number of loops 428.

In the expanded configuration shown in FIG. 4A, the wires 426 can cross at a braid angle θ selected to mitigate kinking and provide adequate extension/constriction. Lower braid angles θ can reduce or eliminate kinking of the wires 426 when the frame 104 is flexed or bent. For example, a braid angle θ of less than 45° allows the frame 104 to bend with smaller radii of curvature without substantial reduction of its cross-sectional area along the length of the frame 104. Therefore, a frame 104 with a braid angle θ of less than 45° can be flexed and bent within the anatomy (e.g., the aorta) without restricting blood flow through the frame 104. Additionally, lower braid angles θ can increase the outward spring force (i.e., the inherent force within the frame 104 that self-expands the frame 104 to the expanded configuration) and hoop strength (i.e., the radial strength of the frame 104 that restricts kinking and maintains the expanded configuration) of the frame 104. Therefore, braid angles θ of not more than 45° can also provide an advantageous increase in the strength and corresponding durability of the frame 104.

Lower braid angles θ, however, can also adversely affect the extension and constriction of the frame 104 in the low-profile configuration shown in FIG. 4B. For example, extension and constriction can be negatively impacted at braid angles θ of less than 30°. Therefore, in some embodiments, the frame 104 can include a braid angle θ between 30° and 45° that promotes kink resistance and frame strength, while also maintaining extension and constriction abilities necessary for the low-profile configuration. In other embodiments, the optimal braid angle θ can be higher or lower.

In some embodiments in accordance with the technology, the braid angle θ can vary along the length of the frame 104 to vary kink resistance, outward spring force, hoop strength, and extension properties at different portions of the frame 104. For example, the braid angle θ can be higher at the superior portion 108 (e.g., 40°) such that the superior portion 108 can extend and constrict into the low-profile configuration, and the braid angle θ can be lower at the inferior portion 110 (e.g., 30°) to provide kink resistance where the frame 104 is most likely to bend (e.g., within the aneurysmal sac and toward the iliac arteries). The smaller braid angle θ at the inferior portion 110 may not adversely affect the profile of the frame 104 because the inferior portion 110 need not constrict as much as the superior portion 108 to reach the desired low-profile configuration. In other embodiments, the braid angle θ of the frame 104 may vary in another way.

The wires 426 can have a diameter sufficient to support the frame 104 while still providing substantial flexibility for the frame 104. The diameter of the wires 426 can be selected to attain a desired cross-sectional dimension in the low-profile configuration, a desired outward spring force to self-expand to the expanded configuration, and a desired hoop strength to support the frame 104 in the expanded configuration. For example, in some embodiments, the wires 426 can have a diameter from approximately 0.007 inch to approximately 0.014 inch. In specific embodiments, the wires have a diameter from approximately 0.011 inch to 0.013 inch. In other embodiments, the wires 426 can have a smaller diameter, a greater diameter, and/or the diameter of the wires 426 can vary along the length of the frame 104. For example, in one embodiment, the wires 426 can have a greater diameter at the superior portion 108 than at the inferior portion 110 such that the wires 426 of the superior portion 108 have a outward spring force and greater hoop strength where the first and second endograft devices mate (e.g., at the septal walls 114) and the increased density of wires 426 at the inferior portion 110 does not negatively impact the flexibility of the frame 104.

The frame 104 may be constructed from a variety of resilient metallic materials, polymeric materials (e.g., polyethylenes, polypropylenes, Nylons, PTFEs, and the like), and composites of materials. For example, the wires 426 can be made from biocompatible stainless steels, highly elastic metallic alloys, and biocompatible shape setting materials that exhibit shape memory properties. In some embodiments, for example, the wire 426 can be made from a shape setting alloy, such as Nitinol, that has a preferred or native configuration. For example, a Nitinol structure can be deformed or constrained into a secondary configuration, but upon release from the constraint, the structure returns toward its native configuration with high fidelity. Accordingly, a frame 104 made from Nitinol wires 426 can reliably self-expand from the low-profile configuration the expanded configuration (i.e., its native configuration).

For endovascular delivery of a device (e.g., the endograft devices 102 shown in FIGS. 1A and 1B), the frame 104 is extended to constrict the frame 104 into a low-profile configuration in which the frame 104 can be loaded into a delivery device. The braid angle θ of the wires 426 can facilitate significant extension of the frame 104 to produce a slender profile during delivery as described above, and yet the interwoven characteristic of the braid restricts over extension. This extension-constriction functionality of the frame 104 allows the frame 104 to have variable diameters (e.g., the diameter of the superior portion 108 compared to the diameter of the inferior portion 11) using the same number of wires 426 on each portion of the frame 104 such that the frame 104 has a low introduction profile (e.g., diameter) along the length of the frame 104. The frame 104 can also include an optimal number of loops 428 at each end portion 118 such that the loops 428 do not increase the profile of the frame 104 upon full extension.

At a target site (e.g., above an aneurysm), the frame 104 self-expands to the expanded configuration shown in FIG. 4A as it is removed from the delivery device. The braid angle θ can be adjusted to change the outward spring force and hoop strength of the expanded frame 104 as explained above. In some circumstances, the endograft device may need to be repositioned after being partially deployed. The frame 104 is well suited for such repositioning because the loops 428 and the continuous, interwoven wires 426 can simplify recapture of the frame 104 and allow for constriction after expansion to correctly reposition the endograft device. Additionally, portions of the frame 104 can remain exposed (e.g., the end portions 118) to encourage cell ingrowth for securely anchoring the frame 104 to the arterial walls. Moreover, as described in more detail below, the interwoven wires 426 of the braided frame 104 can provide a continuous longitudinal support along the length of the frame 104 such that the frame 104 can be staggered and free end portions can support themselves. The frame 104 can also facilitate attachment to other endograft devices. For example, the frame 104 can interlace with another interwoven wire 426 of a supra-renal endograft.

Once deployed across the aneurysm, the frame 104 can also accommodate disparate anatomies and morphologies. In several patients, the aneurysmal sac extends at an angle with respect to the neck of the aneurysm. Because the frame 104 can have a braid angle θ that prevents kinking, the frame 104 can bend and flex without kinking to accommodate angulated aneurysmal sacs without restricting blood flow. Additionally, the unbound, woven wires 426 give the frame 104 a radial elasticity such that the frame 104 mimics the changes in the shape and morphology of the aorta without hindering the interface or seal between the endograft device and the vessel wall. For example, the frame 404 can constrict and expand to maintain the seal when pressure and other conditions alter the vasculature of the aorta. Moreover, the woven wires 426 inherently generate a spring force that biases the frame 104 toward a substantially straight trajectory within an aneurysmal sac and thereby limits migration of the endograft device.

In addition, the constant outward spring force and hoop strength of the braided frame 104 can be adjusted by changing the braid angle θ and/or the diameter of the wires 426. This allows the formation of large diameter frames 104 without a significant change in the low-profile cross-sectional dimensions. Additionally, this feature allows the frames 104 to contract to a much smaller introduction profiles (e.g., diameters) compared to standard Z-frames or M-frames because the standard Z-frames and M-frames tend to require more wire and therefore larger introduction profiles to maintain a constant outward spring force and hoop strength.

2.2 Covers

FIGS. 5A-C are views of a cover being extended from an expanded configuration (FIG. 5A) to a low-profile configuration (FIG. 5C) in accordance with embodiments of the technology. More specifically, FIG. 5A is a side view of the cover 106 described above with reference to FIGS. 1A and 1B in the expanded configuration. The cover 106 can include a plurality of circumferential ribs 530 such that the cover 106 has an undulating profile. As shown in FIG. 5A, the individual ribs 530 can have a substantially triangular shape with an apex 533. In other embodiments, the individual ribs 530 have rounded edges, rectangular edges, and/or other suitable textures that can extend and contract.

The ribs 530 of one cover can mate with opposing ribs 530 of an opposing cover and interface with vessel walls to enhance the seal and fixation between endograft devices in an endograft system (e.g., the endograft devices 102 of the endograft system 100 shown in FIGS. 1A and 1B) and between the endograft devices and the arterial walls. For example, the apices 533 of the ribs 530 at the septal wall 114 of the superior portion 108 of one endograft device can interface or mate with the troughs of the corresponding ribs 530 on a cover of an opposing endograft device. Additionally, the ribs 530 at the outer wall 112 can contact the arterial walls in a manner that at least substantially seals them together. The ribs 530 can also allow the cover 106 to flex and bend without wrinkling in situ. In some embodiments, the ribs 530 can be at only selected portions of the cover 106 (e.g., the septal wall 114). In other embodiments, the ribs 530 can have different shapes and/or geometries on different portions of the cover 106. For example, the apices 533 of the ribs 530 can have a first height on the superior portion 108 to enhance sealing forces between the endograft devices and a second height less than the first height at the inferior portion 110 to allow the cover 106 to freely flex and bend to accommodate the anatomy.

The ribs 530 change with the expansion and contraction of the cover 106. As shown in FIG. 5A, the apices 533 of the ribs 530 protrude to the maximal extent in the expanded configuration. Referring to FIG. 5B, as the cover 106 extends, the ribs 530 also extend and constrict. When the cover 106 is fully extended in the low-profile configuration shown FIG. 5C, the ribs 530 are completely elongated and constricted. In some embodiments, the size of each rib 530 can be predetermined to ensure the ribs 530 are completely flattened in the low-profile configuration and project radially outwardly to interface with adjacent surfaces in the expanded configuration. Accordingly, the ribs 530 do not limit the mobility of the endograft device as it is delivered to the aorta in the low-profile configuration.

Additionally, as shown in FIGS. 5A-C, the cover 106 can include zigzagged edges at a superior terminus 531a and an inferior terminus 531b of the cover 106. The zigzagged termini 531 can facilitate substantially seamless attachment between the cover 106 and an integrated frame (e.g., the frame 104 shown in FIGS. 4A and 4B). For example, in some embodiments, the zigzagged termini 531 can correspond to the braid angle θ of interwoven wires. The zigzagged termini 531 generally prevent the cover 106 from wrinkling or bunching at first and second end portions (e.g., the first and second end portions 118a and 118b shown in FIGS. 4A and 4B) when the cover 106 and the frame are constricted. In other embodiments, the superior and inferior termini 531a and 531b can be scalloped, straight, and/or have another suitable shape that facilitates attachment and/or limits wrinkling.

The cover 106 can be made from a substantially impermeable, biocompatible, and flexible material. For example, the cover 106 can be made from synthetic polymers, polyurethanes, silicone materials, polyurethane/silicone combinations, rubber materials, woven and non-woven fabrics such as Dacron®, fluoropolymer compositions such as a polytetrafluoroethylene (PTFE) materials, expanded PTFE materials (ePTFE) such as TEFLON®, GORE-TEX®, SOFTFORM®, IMPRA®, and/or other suitable materials. Additionally, in some embodiments, the cover 106 can be made from a material that is sufficiently porous to permit ingrowth of endothelial cells. Such a porous material can provide more secure anchorages of endograft devices and potentially reduce flow resistance, sheer forces, and leakage of blood around the endograft devices.

In some embodiments in accordance with the technology, the cover 106 may also include drug-eluting coatings or implants. For example, the cover 106 can be coated and/or imbedded with a slow-releasing drug that can block cell proliferation, promote reendothelialization of the aneurysm, and/or otherwise medicate the aneurysmal region. Suitable drugs can include calcium, proteins, mast cell inhibitors, and/or other suitable medicines that encourage beneficial changes at the aneurysmal region.

In accordance with other embodiments of the technology, the cover 106 can be eliminated in favor of one or more layers of a coating material (shown and described in more detail with reference to FIGS. 17A-E). The coating layer can be made from a biocompatible synthetic polymer, such as PTFE. The coating layer can be placed on the interior of an integrated frame (e.g., the frame 104 shown in FIGS. 4A and 4B), the exterior of the frame, and/or interwoven throughout the frame. Like the cover 106, the coating layers can encase the frame to form a lumen (e.g., the lumen 116 shown in FIGS. 1A and 1B). Additionally, the coating can have a selected porosity that encourages tissue ingrowth.

2.3 Integrated Frame and Cover

FIGS. 6A and 6B are cross-sectional views of the endograft device 102 of FIGS. 1A and 1B in a low-profile configuration and an expanded configuration, respectively, in accordance with embodiments of the technology. As shown in FIGS. 6A and 6B, the cover 106 can be attached to the exterior of the frame 104 at one or more attachment areas 632 (identified individually as a first attachment area 632a and a second attachment area 632b). The attachment areas 632 can have sutures, adhesives, welds, and/or other suitable fasteners that discretely hold the cover 106 to the frame 104 at the attachment areas 632.

In the embodiment shown in FIGS. 6A and 6B, the endograft device 102 has attachment areas 632 at only the superior and inferior termini 531a and 531b of the cover 106 such that the remainder of the cover 106 between the attachment areas 632 is not attached directly the frame 104. As a result, the frame 104 and the cover 106 can fully extend and constrict as shown in FIG. 6A without interfering with one another. For example, in the low-profile configuration shown in FIG. 6A, the frame 104 does not directly pull the central portion of the cover 106 downward and longitudinally with the frame 104 such that the ribs 530 can stretch uniformly along the length of the cover 106 to accommodate full extension of the frame 104. Similarly, the intermediate portions of the cover 106 do not hinder the extension or constriction of the frame 104. Fewer attachments areas 632 can also limit the potential for fatigue and undesirable porosity that may arise at the attachment areas 632, such as from needle pricks and other fastening mechanisms that puncture the cover 106.

As shown in FIG. 6B, the cover 106 can substantially conform to the shape of the frame 104 when they are in the expanded configuration. Proper alignment between the cover 106 and the frame 104 prevents the cover 106 from adversely affecting constriction and expansion. For example, alignment between the cover 106 and the frame 104 at the superior and transition portions 108 and 324, respectively, ensures the frame 104 can expand properly and generate the force necessary to mate with a superior portion of an opposing endograft device. Additionally, in some embodiments, the cover 106 is sized to restrict the expansion and corresponding contraction of the frame 104.

Attaching the cover 106 to the exterior of the frame 104 as shown in FIGS. 6A and 6B can provide a plurality of benefits for the endograft device 102. For example, unlike endograft devices with internal covers that must fold within a frame during delivery, the exterior cover 106 does not inhibit constriction of the frame 104 (e.g., FIG. 6A). In the expanded configuration, the exterior the cover 106 does not bunch or wrinkle within the frame 104, and thus does not cause thrombotic problems within the lumen 116. Additionally, unlike more rigid Z-stents, the flexibility of the frame 104 can prevent abrasive rubbing and deterioration of the cover 106 in the expanded configuration (e.g., FIG. 6B). The exterior attachment of the cover 106 can also prevent over expansion of the frame 104.

2.4 Alignment Aids

Figure 7A:
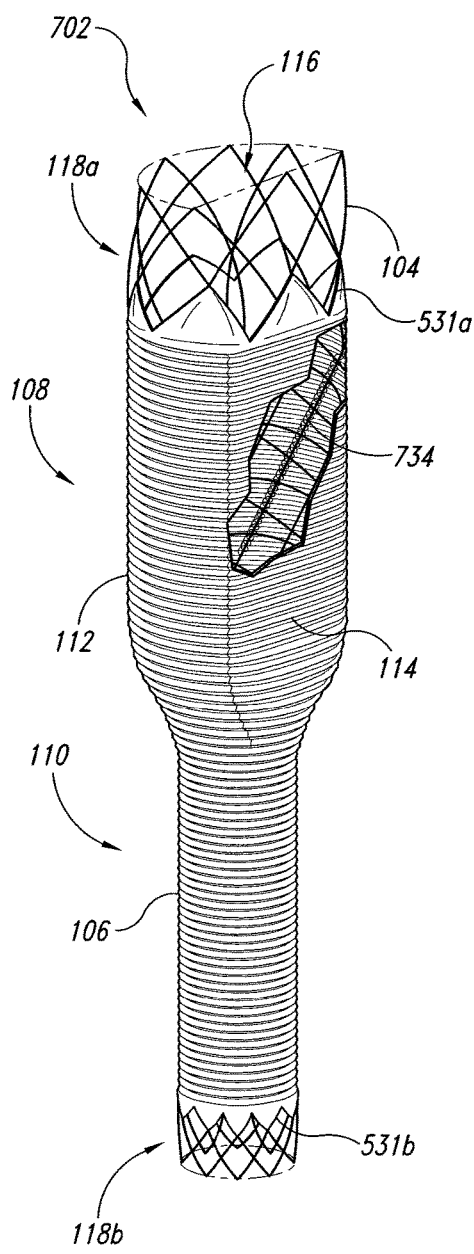
FIGS. 7A and 7B are isometric views of endograft devices configured in accordance with other embodiments of the technology.
Figure 7B:
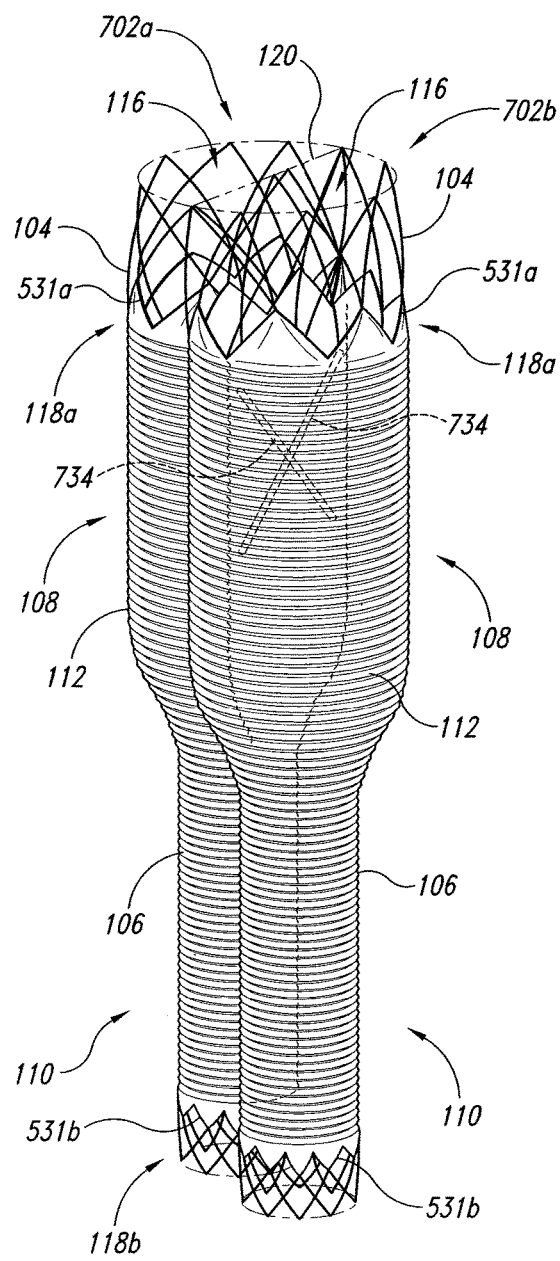

FIGS. 7A and 7B are isometric views of endograft devices 702 in accordance with additional embodiments of the technology. The endograft devices 702 can have generally similar features as the endograft devices 102 shown in FIGS. 1A and 1B. Additionally, the endograft devices 702 can include alignment aids 734 that are visible under imaging systems (e.g., X-rays) to facilitate accurate positioning and subsequent monitoring of the endograft devices 702 in the vasculature.

FIG. 7A is a partial cut-away isometric view of the endograft device 7-2 showing an alignment aid 734 in accordance with an embodiment of the technology. As shown in FIG. 7A, the alignment aid 734 can extend diagonally along the septal wall 114 of the frame 104 to indicate the position of the septal wall 114 relative to the endograft device 702. The alignment aid 734 can thus provide an indication of the rotational orientation and axial location of the endograft device 702 such that during deployment opposing septal walls 114 can be properly aligned and mated with one another. Additionally, as shown in the embodiment in FIG. 7A, the alignment aid 734 can terminate at the superior terminus 531a of the cover 106 to indicate where the first end portion 118a begins. Thus, the alignment aid 734 provides a definitive indicator to ensure that the cover 106 does not block transverse flow (e.g., from the aorta to the renal arteries). In other embodiments, the alignment aids 734 may be positioned elsewhere along the endograft device 702 to provide spatial location and orientation that can aid delivery and deployment of the endograft device 702.

The alignment aid 734 can be made from radiopaque and/or fluoroscopic materials, such as tantalum, platinum, gold, and/or other materials that are visible under an imaging system (e.g., X-rays). For example, as shown in FIG. 7A, the alignment aid 734 is made from a radiopaque wire (e.g., tantalum) wound around a segment of the frame 104. In another embodiment, a radiopaque composition is applied to the frame 104 and/or incorporated in the septal walls 114 of the cover 106.

FIG. 7B shows the first and second endograft devices 702 mated together using the alignment aids 734 in accordance with an embodiment of the technology. As shown in FIG. 7B, the alignment aids 734 on the first and second endograft devices 702a and 702b are symmetrical such that when the endograft devices 702 are correctly oriented and the septal walls 114 oppose one another, the alignment aids 734 can intersect to form an "X" indicator. In other embodiments, the intersection of the alignment aids 734 forms other characters, numbers, and/or symbols that indicate the rotational orientation and longitudinal location of the endograft devices 702. In further embodiments, the alignment aids 734 can be applied to different portions of the septal wall (e.g., the cover 102) and/or the outer wall 112. In still further embodiments, the endograft devices 702 include a plurality of alignment aids 734 to distinguish different portions of the endograft devices 702 and further aid rotational and/or other orientation. For example, in some embodiments, the inferior portions 110 include alignment aids 734 that differentiate the inferior portions 110 of the first and second endograft devices 702.

2.5 Anchors

Figure 8A:
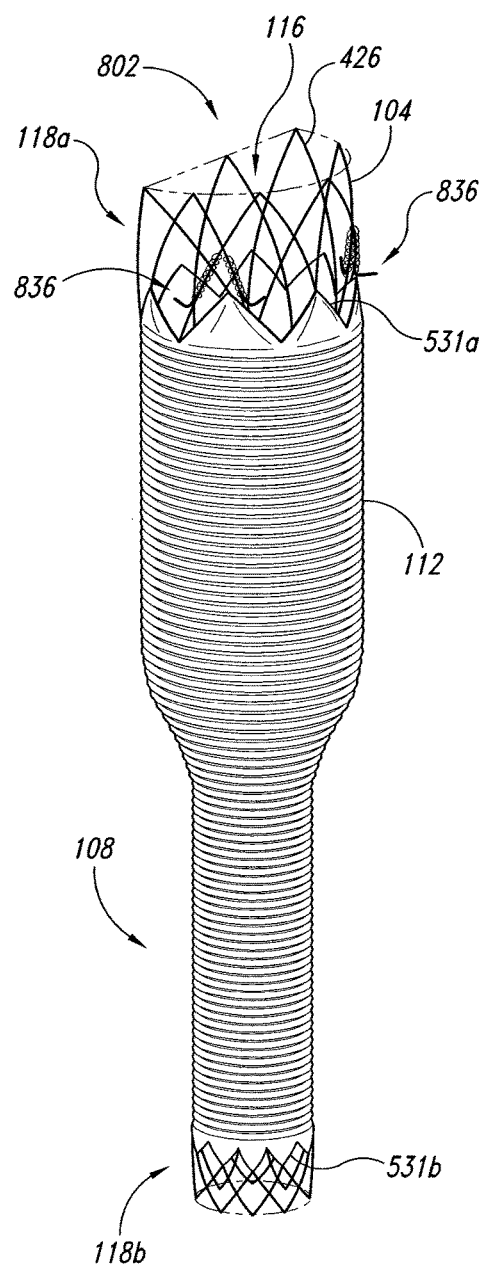
FIGS. 8A and 8B are isometric views of endograft devices configured in accordance with further embodiments of the technology.
Figure 8B:
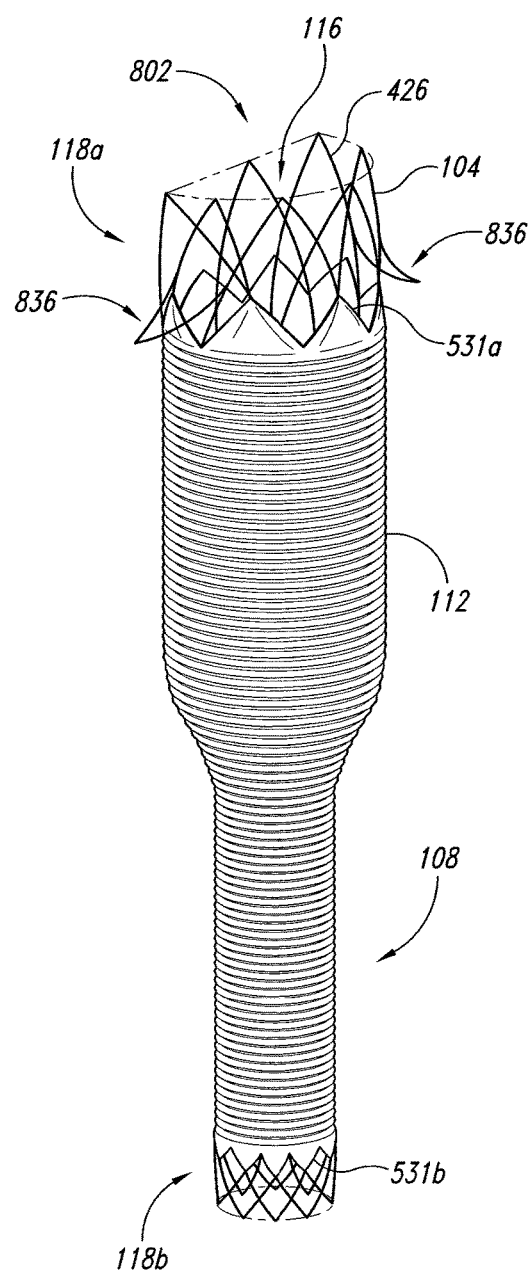

FIGS. 8A and 8B are isometric views of endograft devices 802 configured in accordance with additional embodiments of the technology. The endograft devices 802 can include generally similar features as the endograft devices 102 shown in FIGS. 1A and 1B. Additionally, the endograft devices 802 can include one or more anchors 836 that project outwardly from the frame 104 and/or cover 106 to engage the interior surfaces of arterial walls. The anchors 836 can be barbs, hooks, and or other shapes that can penetrate into the arterial walls. For example, as shown in FIG. 8A, the anchors 836 can be "V" shaped projections. In some embodiments, the anchors 836 eventually become embedded in cell growth on the interior surface of the arterial wall. In operation, the anchors 836 resist migration of the endograft devices 802 within the artery and reduce the likelihood of endoleaks between the outer wall 112 and the arterial wall.

In an embodiment shown in FIGS. 8A and 8B, the anchors 836 project from the outer walls 112 to secure the superior portions 108 to the aorta. In other embodiments, additional anchors 836 can project from the second end portions 118b to secure the inferior portions 110 to the iliac arteries. The anchors 836 can also protrude from the septal walls 114, extend through the lumen 116, and project outward beyond the outer wall 112 to enhance the strength of the engagement. The anchors generally project inferiorly such that downward forces applied to the endograft devices 802 (e.g., blood flow) drive the anchors 836 further into the arterial walls.

In one embodiment in accordance with the technology, the anchors 836 are separate elements that are attached to the frame 104. For example, in the embodiment shown in FIG. 8A, the anchors 836 are small barbs or wires that are fastened to the frame 104 by winding another wire (e.g., a Nitinol wire) around the anchors 836 and the adjacent wire 426 of the braid. In other embodiments, the anchors 326 are integrally formed with the wire 426 used in the braid of the frame 104. For example, as shown in FIG. 8B, the anchors 836 are woven into the outer wall 112 of the frame 104. The interwoven anchors 836 can be deployed (i.e., project outwardly) when the frame 104 expands and can retract when the frame 104 constricts. Accordingly, the interwoven anchors 836 do not inhibit movement of the endograft device 802 during delivery in the low-profile configuration. In other embodiments, the anchors 836 can be attached to a different portion of the endograft device 802 (e.g., the cover 106).

The anchors 836 can be made from resilient metallic materials, polymeric materials (e.g., polyethylenes, polypropylenes, Nylons, PTFEs), and/or other suitable materials that can anchor the endograft devices 802 to arterial walls. For example, the interwoven anchors 836 shown in FIG. 8B can be made from Nitinol wire 426 that comprises the frame 104.

3. Methods of Implementation and Assembled Endograft Systems

Described below are methods of deploying and assembling modular endograft systems across an aneurysm in accordance with embodiments of the technology. The associated Figures (i.e., FIGS. 9A, 9B, 11-13C and 15A-16) include schematic representations of an abdominal portion of an aorta. More specifically, FIG. 9A shows an aneurysm 50 located along an infrarenal portion of the aorta 52, which is the most common site of an AAA. A right or first renal artery 54a and a left or second renal artery 54b stem from the aorta 52. The region of the aorta 52 superior to the aneurysm 50 and inferior to the renal arteries 54 is the aortic neck 60. The distal end portion of the aorta 52 bifurcates into common iliac arteries 56 (identified individually as a first iliac artery 56a and a second iliac artery 56b), and the internal iliac arteries 58 (identified individually as a first internal iliac artery 58a and a second internal iliac artery 58b) branch from the common iliac arteries 56. Other arteries and structures proximate to the abdominal portion of the aorta 52 have been removed for clarity.

3.1 Modular Endograft Systems

FIGS. 9A and 9B are schematic views of the two-part modular endograft system 100 described above being deployed across the aneurysm 50 in accordance with an embodiment of the technology. FIG. 9A shows a delivery system 40 for implanting the first and second endograft devices 102a and 102b. The delivery system can include a first catheter 42a, a first guidewire 44a associated with the first catheter 42a, a second catheter 42b, and a second guidewire 44b associated with the second catheter 42b. Each endograft device 102 (FIG. 9B) can be extended to the low-profile configuration and loaded into the corresponding catheter 42. Because the endograft devices 102 are delivered separately, the sizes of the catheters 42 are not constrained by the system 100 as a whole. In some embodiments, for example, the low-profile configurations of each endograft device 102 can fit within a 12 F catheter. In other embodiments, the low-profile configuration of the endograft devices 102 can fit within differently sized catheters 42.

During deployment, the first catheter 42a and the first guidewire 44a are inserted percutaneously into a blood vessel (e.g., a femoral artery; not shown). With the aid of imaging systems, the first guidewire 44a is endoluminally navigated through the vasculature, up the first iliac artery 56a, and to a location superior to a target site T above the aneurysm 50. The first catheter 42a is then passed through the vasculature along the first guidewire 44a to the target site T. Using a generally similar method, the second guidewire 44b and the second catheter 42b are delivered through the second iliac artery 56b to the target site T. The first and second endograft devices 102a and 102b can be delivered simultaneously or in succession.

The endograft devices 102 can be urged out of the distal ends of the catheters 42 at the target site T by withdrawing the catheters 42 proximally while holding the endograft devices 102 in place using pushers or other suitable endovascular instruments. Alternatively, the endograft devices 102 can be pushed distally while holding the catheters 42 in place. Upon release, the endograft devices 102 self-expand to the expanded configuration shown in FIG. 9B. The guidewires 44 generally remain in place to facilitate adjusting the endograft devices 102. This eliminates the need to cannulate either of the endograft devices 102.

Each endograft device 102 can be positioned at its desired location independently of the other endograft device 102 while the endograft devices 102 are in, or at least partially within, the catheters 42. For example, in the embodiment illustrated in FIG. 9B, the superior portions 108 contact the aortic neck 60 at the same level, and the inferior portions 110 extend through the aneurysm 50 to their respective iliac arteries 56. More specifically, the inherent hoop force of the frame 104 caused by the constant outward spring force of the braid at least substantially seals (a) the covers 106 at the outer walls 112 against the aortic neck 60 and (b) the septal walls 114 to each other to form the septum 120. The inferior portions 110 extend through the aneurysm 50 and can bend to enter the iliac arteries 56. The proximal portion of the inferior portions 110 contact the iliac arteries 56 and can form a seal therebetween. The flexibility of the frame 104 prevents the endograft devices 102 from kinking at the bend and restricting blood flow. Additionally, as shown in FIG.

9B, the spring force within the frame 104 biases the inferior portions 110 to extend in a substantially straight trajectory through the aneurysm 50. This inhibits migration of the inferior portions 110 to a side of the aneurysm 50 that could break the contact and/or seal at the aortic neck 60. As described in more detail below, in other embodiments the endograft devices 102 can be positioned independently at different elevations along the aortic neck 60.

As further shown in FIG. 9B, the endograft system 100 can include extension units 937 (identified individually as a first extension unit 937a and a second extension unit 937b) projecting distally from the superior termini 531 of the covers 106. The extension units 937 can include an extension frame 904 (not visible) and an extension cover 906 at least generally similar to the frame 104 and the cover 106 of the endograft devices 102 described above. The extension units 937 can have a substantially similar shape as the superior portions 108 of the endograft devices (e.g., a D-like shape) such that the extension units 937 can mate with the interior of at least a part of the superior portions 108. For example, as shown in FIG. 9B, the extension covers 906 can be positioned inferior to the renal arteries 54 within the frame 104 such that the extension covers 906 can interface with the aortic neck 60 and mate with one another to extend the septum 120 distally. Therefore, the extension units 937 can increase the fixation area and the sealing area of the endograft devices 102 when the superior termini 531 of the covers 106 of the endograft devices 102 are offset from the entrances of the renal arteries 54. For example, in some embodiments, the extension units 937 add approximately one inch of fixation structure and sealing area to the endograft devices 102. In other embodiments, the inferior portions 110 can also include extension units 937 that can affix and at least substantially seal to the iliac arteries 56.

During deployment, the extension units 937 can be added to the system 100 after the first and second endograft devices 102 are positioned within the aortic neck 60. With the aid of the delivery system 40, the extension units 937 can advance along the guidewires 44 and be deployed from the catheters 42 at desired positions within the first and second frames 104 just inferior of the renal arteries. Upon deployment, the extension units 937 can self-expand via an inherent spring force in the extension frame 904 to an expanded configuration to contact and at least substantially seal with the interior of the superior portions 108 of the endograft devices 102. As shown in FIG. 9B, the extension cover 906 can interface with the first end portions 118a of the frames 104 to strengthen the seal therebetween. In other embodiments, the extension units 937 can connect and seal to the endograft devices 102 using other suitable attachment methods. The extension units 937 can be positioned independently such that they accommodate anatomical variations (e.g. staggered renal arteries). For example, a superior terminus of the first extension unit 937a can be longitudinally offset from a superior terminus of the second extension units 937b. Similarly, the inferior portions 110 can include extension units 937 that increase the sealing area with the iliac arteries 56.

In some embodiments, alignment aids, such as the alignment aids 734 described with reference to FIGS. 7A and 7B, are used to rotationally orient the endograft devices 102 and align the septal walls 114 during delivery. Additionally, to prevent migration and/or projection of the system while in situ, anchors, such as the anchors 836 described above with reference to FIGS. 8A and 8B, can be deployed from the outer walls 112 to engage the arterial walls of the aortic neck 60 and/or from the second end portions 118b to engage the arterial walls of the iliac arteries 56.

Figure 10A:
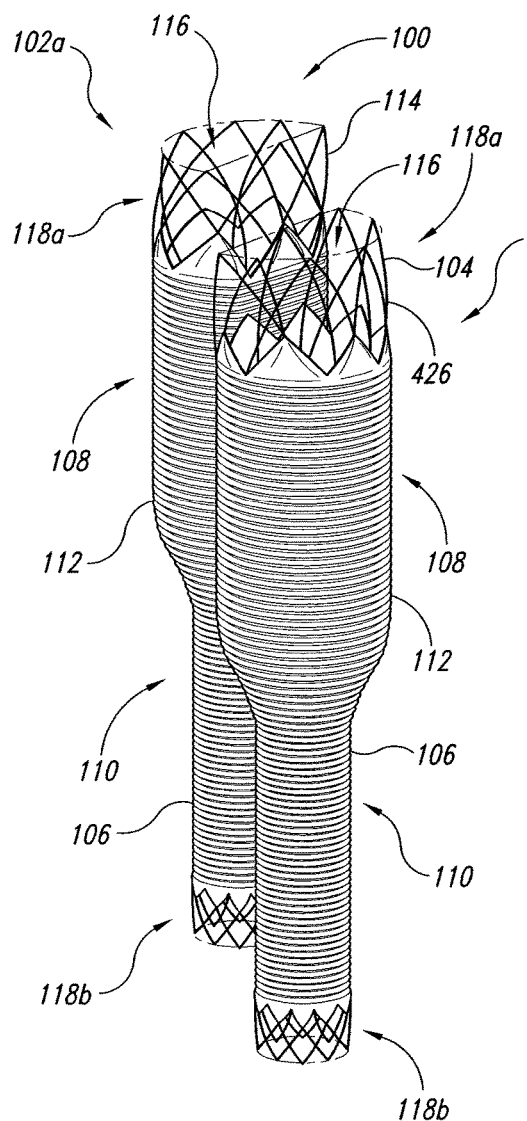
FIGS. 10A and 10B are isometric views of modular endograft systems configured in accordance with additional embodiments of the technology.

FIGS. 10A-11 show additional embodiments of implementing endograft systems (e.g., the system 100) in which the superior portions 108 are longitudinally offset from each other. For example, in some embodiments, the superior portions 108 are longitudinally offset by at least 5 mm. The features of the systems below allow one or both of the superior portions 108 to be placed over transverse arteries to increase the available fixation structure and sealing area for the endograft devices 102 without inhibiting blood flow.

FIG. 10A is an isometric view of the modular endograft system 100 in which the endograft devices 102 are staggered such that the superior portion 108 of the first endograft device 102a is above the superior portion 108 of the second endograft device 102b. The first end portion 118a of the second endograft device 102b can prevent the unsupported free first end portion 118a of the first endograft device 102a from splaying outward into the blood flow in a manner that induces undo turbulence. Moreover, the interplay between the woven wires 426 of the frame 104 of the first endograft device 102a restricts the outward movement of the first end portion 118a of the first endograft device 102a and provides substantially continuous support along the length of the frame 104 such the free first end portion 118a retains substantially the same shape as if it were supported. These features maintain the generally straight or convex shape of the unsupported septal region of the first portion 118a of the first endograft device 102a. Using shape-setting Nitinol wire 426 in the frame 104 can further facilitate maintaining the shape of the unsupported portion of the frame 104.

Compared to conventional devices that have a common height across the diameter of a vessel (e.g., the aorta), the staggered configuration shown in FIG. 10A allows one or both of the first end portions 118a to extend over the entrance of the renal arteries to increase the available structure for fixing the endograft devices 102 to the vessel wall. The staggered configuration also increases the sealing area of the superiorly positioned first endograft device 102a for anatomies having a short aortic neck (e.g., less than 2 cm). Similarly, the second end portions 118b can extend over the entrances of the internal iliac arteries to ensure the inferior portions 110 each have an adequate structure for fixing and at least substantially sealing the inferior portions 110 to the iliac arteries. To the extent migration occurs, the additional sealing area between the endograft devices 102 and the vessel walls will reduce the potential for leakage at the aortic neck.

Figure 10B:
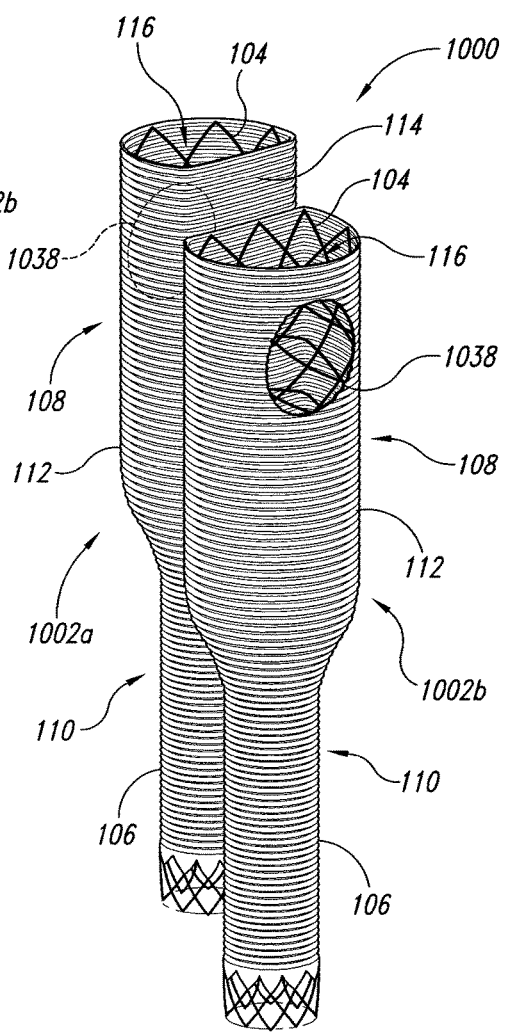

FIG. 10B is an isometric view of a modular endograft system 1000 configured in accordance with an additional embodiment of the technology. The system 1000 can have a first endograft device 1002a and a second endograft device 1002b that are generally similar to the endograft devices 102 described above. The covers 106 of the endograft devices 1002 in FIG. 10B, however, extend to the distal ends of the superior portions 108. Additionally, the endograft devices 1002 further include fenestrations 1038 on the outer walls 112 of the superior portions 108.

The fenestrations 1038 can be openings through the cover 106 that expose the frame 104 and provide a channel through which blood can flow to and from transverse arteries. For example, the endograft devices 1002 can be positioned independently and staggered such that the fenestration 1038 of each endograft device 1002 is aligned with one of the left or right renal arteries. The fenestrations 1038 accordingly increase the available sealing area between the outer walls 112 and the arterial walls because the superior portions 108 can be positioned independently over the renal arteries such that one endograft device 1002 does not need to be limited to the elevation of the inferior renal artery. This provides optimal placement for each endograft device 1002 within the vasculature without requiring customized devices. In other embodiments in accordance with the technology, the endograft devices 1002 can include additional fenestrations 1038 to increase the available sealing area without restricting blood flow. For example, the inferior portions 110 can include fenestrations 1038 that allow the inferior portions 110 to extend over the entrance of the internal iliac arteries.

Figure 11A:
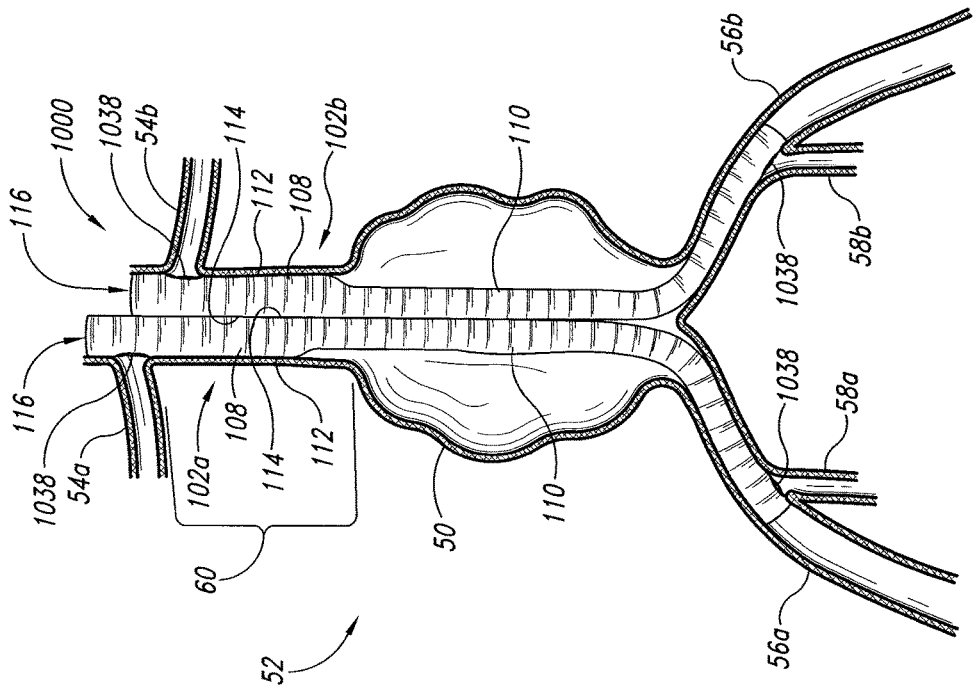
FIGS. 11A and 11B are schematic views of the modular endograft system of FIG. 10A and the modular endograft system of FIG. 10B, respectively, deployed across aneurysms in accordance with other embodiments of the technology.

FIG. 11A is a schematic view of the modular endograft system 100 deployed across an aneurysm such that the superior portions 108 of the endograft devices 102 are staggered to accommodate for anatomical variations in the vasculature in a manner that takes advantage of the available structure for fixing the endograft devices 102 to arterial walls and the available sealing area in the aortic neck 60. In the embodiment shown in FIG. 11A, for example, the left renal artery 54*b* is inferior the right renal artery 54*a*. The first endograft device 102*a* can, therefore, also be positioned higher in the aorta 52 to utilize the available fixation and sealing areas on the ipsilateral side of the aortic neck 60 without having to be concerned about blocking the entrance of the left renal artery 54*b*. The first end portion 118*a* of the second endograft device 102*b* can be positioned over the left renal artery 54*b* without inhibiting blood flow to lengthen the structure for fixing the second endograft device 102*b* to the arterial wall and mating the septal walls 114 together. The longer fixation and sealing areas along the outer wall 112 of the first endograft device 102*a* and the longer mating and sealing areas between the septal walls 114 can strengthen the seals of the system 100 as a whole to reduce the likelihood of endoleaks. Additionally, as shown in FIG. 11A, the system 100 can be staggered to accommodate an anatomy with less fixation and sealing area in one of the iliac arteries 56.

Figure 11B:
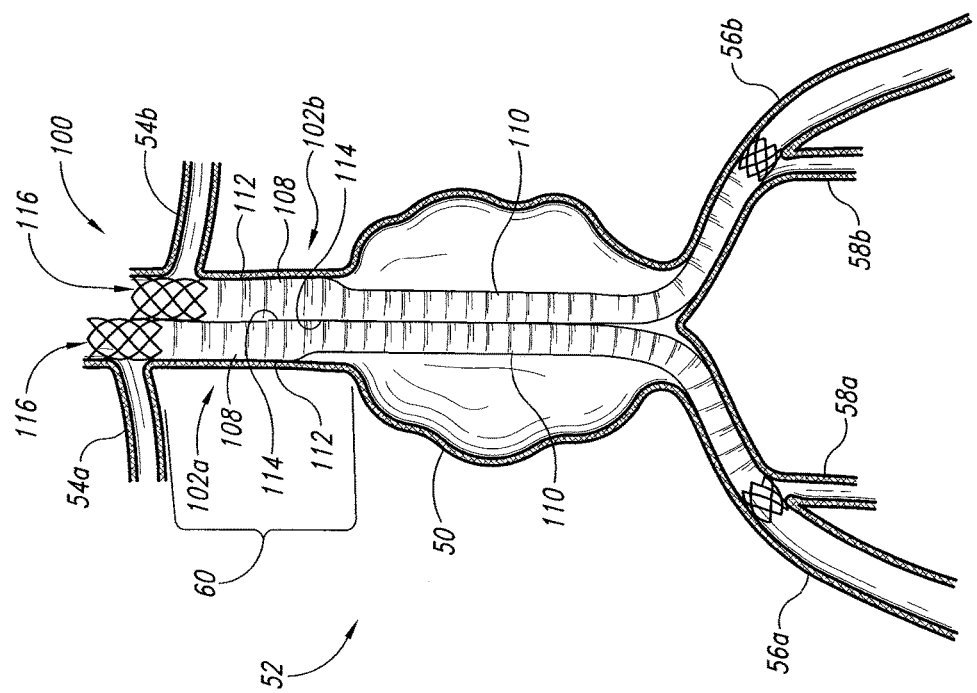

FIG. 11B is a schematic view of the modular endograft system 1000 of FIG. 10B deployed across the aneurysm 60. Similar to the configuration of the system 100 shown in FIG. 11A, the endograft devices 1002 are staggered to accommodate for anatomical variations in the vasculature in a manner that takes advantage of the available anatomical structure for fixing and sealing the outer walls 112 of the endograft devices 102 to the arterial walls in the aortic neck 60. As shown in FIG. 11B, for example, the first endograft device 1002*a* can be positioned superior to the second endograft device 1002*b* in the aortic neck 60 to utilize the available fixation and sealing area on the ipsilateral side of the aortic neck 60. The fenestrations 1038 can be placed independently at the entrance of each renal artery 54 to increase the available fixation and sealing area in the aortic neck 60 and accommodate asymmetrical anatomies. Additionally, as further shown in FIG. 11B, the endograft devices can include fenestrations 1038 at the inferior portions 110 that can be placed independently at the entrance of each internal iliac artery 58 to accommodate an anatomy with less sealing area in the iliac arteries 56. In other embodiments, the endograft devices 102 can include fenestrations 1038 to accommodate other anatomical variations.

Figure 12:
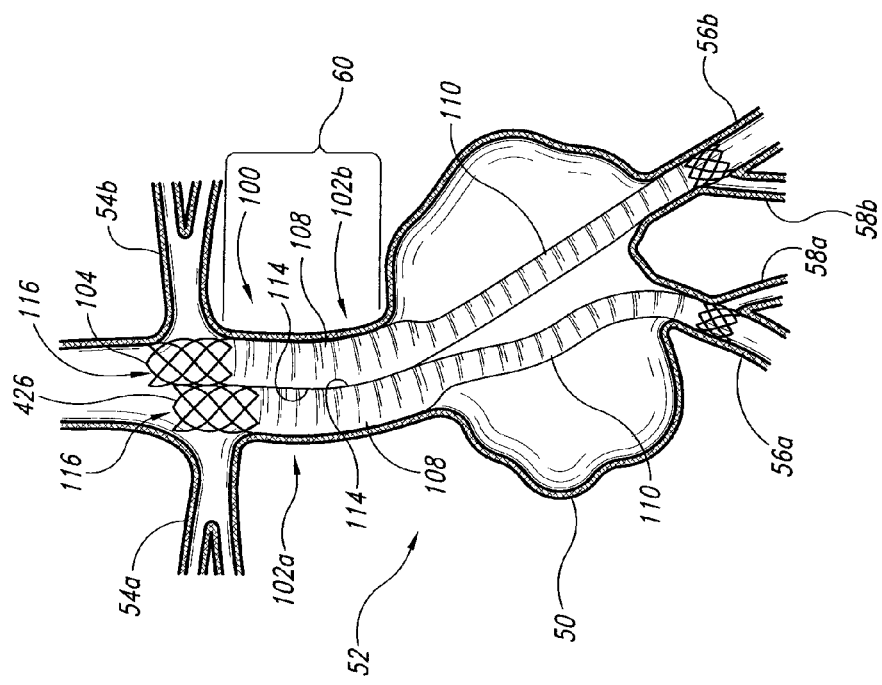
FIG. 12 is a schematic view of the modular endograft system of FIG. 9B deployed across an aneurysm in accordance with a further embodiment of the technology.

FIG. 12 is a schematic view of the modular endograft system of FIGS. 9A and 9B deployed across an angulated aneurysm in accordance with an additional embodiment of the technology. The system 100 can accommodate this anatomical abnormality because the endograft devices 102 are flexible. More specifically, the interwoven wires 426 of the frame 104 are sufficiently flexibility to bend without kinking. Thus, the bent endograft devices 102 can maintain unrestricted flow through the lumens 116. Accordingly, the system 100 can accommodate other anatomical variations that may require the endograft devices 102 to flex or bend without disturbing blood flow.

Figure 13A:
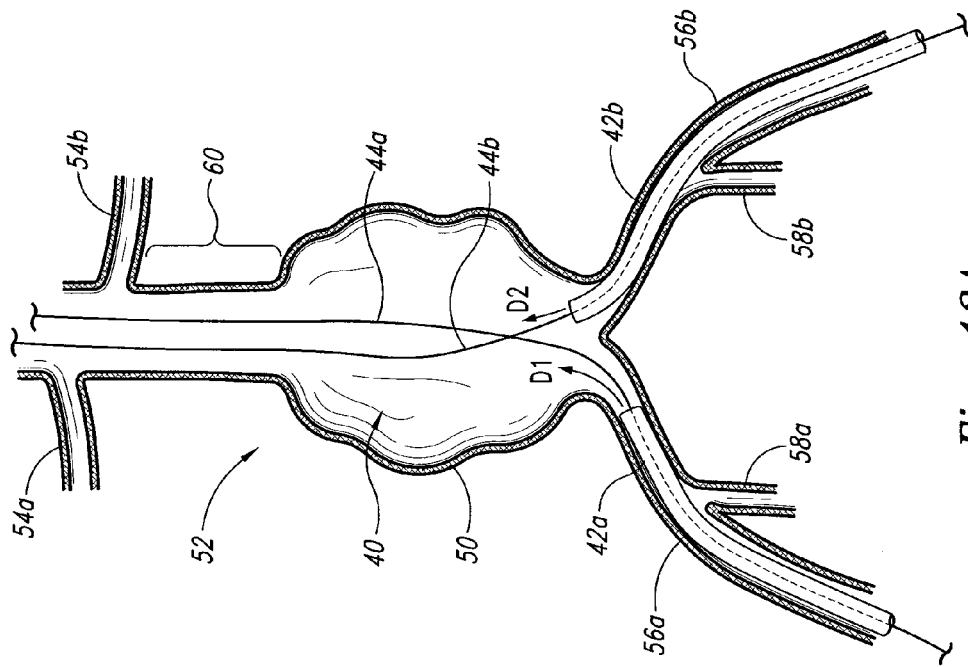

FIGS. 13A-C are schematic views of a four-part modular endograft 1300 system ("system 1300") being deployed across the aneurysm 50 in accordance with an embodiment of the technology. The system 1300 can include generally similar features as the system 100 described with reference to FIGS. 9A and 9B. However, as shown in FIG. 13B, the inferior portions 110 of the endograft devices 102 terminate within the aneurysm 50. Therefore, as shown in FIG. 13C, the system 1300 further includes separate limbs 1362 (identified individually as a first limb 1362*a* and a second limb 1362*b*) that contact and substantially seal with corresponding inferior portions 110 and extend into corresponding iliac arteries 56. The limbs 1362 can be generally similar to the inferior portions 110. For example, the limbs 1362 can include an integrated frame 1304 and a cover 1306 generally similar to the frame 104 and the cover 106 described above with reference to FIGS. 1A-6B. As shown in FIG. 13C, the limbs 1362 self-expand within the interior portions 110 to the expanded configuration and thereby the superior portions of the limbs 1362 at least substantially seals to the proximal section of the inferior portions 110. The length of the limbs 1362 within the inferior portions 110 can be adjusted to increase the available structure for fixing and sealing the limbs 1362 to the endograft devices 102. Additionally, in some embodiments, the covers 1306 of the limbs 1362 can include ribs, such as the ribs 530 described above with reference to FIGS. 5A-C, that interface with the interior of the frames 104 and the covers 106 at the inferior portions 110 to connect and at least substantially seal the limbs 1362 to the inferior portions 110. In other embodiments, the limbs 1362 can connect and at least substantially seal to the exteriors of the inferior portions 110 using anchors (e.g., the anchors 836 described with reference to FIGS. 8A and 8B), self-constricting forces, and/or other suitable attachment and sealing methods. The limbs 1362 extend the lumens 116 of the endograft devices 102 to the iliac arteries 56 such that blood can flow through the system 1300 to bypass the aneurysm 50.

Referring to FIG. 13A, the delivery system 40 is shown within the abdominal portion of the aorta 52 before deploying the endograft system 1300. The insertion of the delivery system 40 can be generally similar as described above with reference to FIG. 9A. However, as shown in FIG. 13A, the first and second guidewires 44*a* and 44*b* can cross after they enter the aneurysm 50 such that each catheter 42 extends from its respective iliac artery 54 to the contralateral side of the aorta 52. For example, the first catheter 42*a* can be delivered from the first iliac artery 56*a* to the left side of the aorta 52 proximate to the left renal artery 54*b* (Arrow $D_1$), and the second catheter 42*b* can be delivered from the second iliac artery 56*b* to the right renal artery 54*a* (Arrow $D_2$). In other embodiments, such as in the deployment method described above with reference to FIGS. 9A and 9B, the guidewires 44 do not cross within the aneurysm 50.

Referring to FIG. 13B, after the first and second catheters 42*a* and 42*b* are positioned in the aortic neck 60, they are pulled proximally to deploy the endograft devices 102 through the distal ends of the catheters 42. The crossing catheters 42 and guidewires 44 deploy the endograft devices 102 on opposite sides of the aortic neck 60.

As shown in FIG. 13B, the inferior portions 110 of the endograft devices 102 terminate within the aneurysm 50 and form a "gate." In general, gates are considered undesirable because in conventional systems they must be cannulated to deliver and deploy limbs that extend the endograft devices into the iliac arteries 56. However, as shown in FIG. 13B, the guidewires 44 remain within the endograft devices 102 after they are deployed; this eliminates the need for time-consuming cannulation of the gates because the inferior portions 110 of the endograft devices 102 are in effect pre-cannulated. Such pre-cannulated gates allow the limbs 1362 to be delivered through the distal ends of the catheters 42 and connected to the inferior portions 110 much faster and more accurately than conventional systems.

FIG. 13C shows the system 1300 after both limbs 1362 are connected to the endograft devices 102. As shown in FIG. 13C, the delivery system 40 can also be used to adjust the length of the limbs 1362 and the length of the fixation area between the limbs 1362 and the inferior portions 110 in the direction of the arrows. In the embodiment shown in FIG. 13C, for example, the second limb 1362b extends further into the inferior portion 110 of the second endograft device 102b such that the second limb 1362b is effectively shorter than the first limb 1362a. The length of the limbs 1362 can be adjusted to accommodate disparate anatomies of the iliac arteries 56, maximize the fixation and sealing areas of the limbs 1362, and/or otherwise optimize the position of the limbs 1362. This is possible because, at least in part, the inferior portions 110 of the endograft devices 102 can be relatively long to allow significant longitudinal leeway in positioning the limbs 1362 while still providing adequate surface area to at least substantially seal the limbs 1362 to the inferior portions 110.

The four-part, two-wire system 1300 can easily accommodate anatomical variations without requiring customized components. For example, the superior portions 108 can be staggered to maximize the mating and sealing area of each outer wall 112 with the aortic walls. Additionally, each limb 1362 can be selected from a relatively small number of different lengths to extend a desired length within the iliac arteries 56 that both adequately connects and substantially seals the limbs 1362 to the arterial walls and does not block transverse arterial flow. The limbs 1362 can also be adjusted independently relative to the inferior portions 110 to increase the available structure for fixing and sealing the limbs 1362 and the inferior portions 110 together, and to shorten or lengthen the limbs 1362 within the iliac arteries 56. Additionally, the braided structure of the frames 104 can decrease infolding of the covers 106 such that the lengths of the frame 104 can be selected from standardized cross-sectional dimensions. Thus, the four-part system 1300 can be highly customizable, but yet comprise standardized components.

3.2 Modular Endocraft System with Aortic Cuff

Figure 14A:
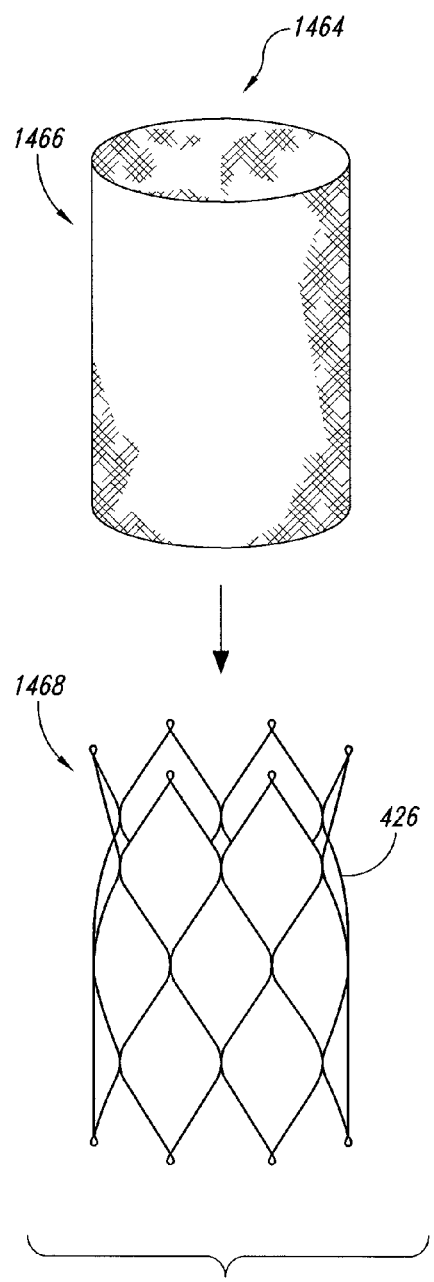
FIGS. 14A and 14B are isometric views of a modular endograft system configured in accordance with an additional embodiment of the technology.
Figure 14B:
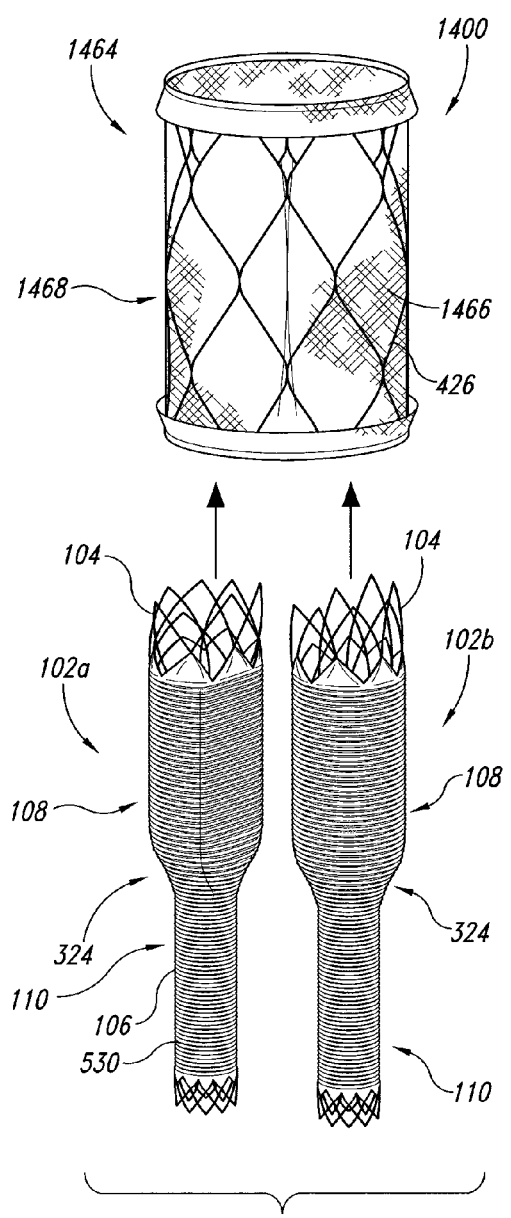

FIGS. 14A and 14B are isometric views of a modular endograft system 1400 ("system 1400" shown in FIG. 14B) configured in accordance with embodiments of the technology. More specifically, FIG. 14A is an isometric view of an aortic cuff 1464 for use with the endograft devices 102 (FIG. 14B). The aortic cuff 1464 can include a sleeve 1466 and a cuff frame 1468. As shown in FIG. 14A, the sleeve 1466 and the cuff frame 1468 can be separate components. In other embodiments, the sleeve 1466 and the cuff frame 1468 can be formed integrally. The aortic cuff 1464 can expand from a low-profile configuration having a first cross-section to an expanded configuration (e.g., FIG. 14B) having a second cross-section larger than the first cross-section. The low-profile configuration can be used during delivery of the aortic cuff 1464 from which the cuff-device 1464 can self-expand to the expanded configuration in situ. The aortic cuff 1464 can be configured to interface and substantially seal with an infrarenal portion of the aorta superior to an aneurysm.

The sleeve 1466 can be attached to the interior and/or exterior of the cuff frame 1468 using suitable fastening methods. For example, as shown in FIG. 14B, the sleeve 1466 is positioned within the interior of the cuff frame 1468, and the ends of the sleeve 1466 extend over and are fixed to proximal and distal ends of the cuff frame 1468 using suitable fastening methods (e.g., stitching, gluing, welding, etc.). In some embodiments, the proximal and distal ends of the cuff frame 1468 can be flared, and the sleeve 1466 can wrap around the flared ends to the exterior of the cuff frame 1468 such that the attachment can be sealed by the arterial walls when the aortic cuff 1464 is expanded to the expanded configuration in situ. The sleeve 1466 can have generally similar characteristics as the cover 106 described above. For example, the sleeve 1466 can be made from one or more substantially impermeable materials, such as Dacron® and PTFE, and can include ribs that can interface with arterial walls and/or endograft devices 102 (FIG. 14B). The cuff frame 1468 can have generally similar characteristics as the integrated frame 104 described above. In other embodiments, the cuff frame 1468 can be made from individual zigzagged wire hoops like a Z-stent.

The sleeve 1466 and the cuff frame 1468 can have a substantially cylindrical shape. In some embodiments, the aortic cuff 1464 can include two channels to support superior portions 108 of endograft devices 102 (FIG. 14B). For example, the channels can be formed by stitching the fabric of the sleeve 1466 together to divide the interior of the aortic cuff 1464. Additionally, the sleeve 1466 and/or the cuff frame 1468 can have flared proximal and distal ends to form a stronger seal with adjacent arterial walls.

Referring to FIG. 14B, the endograft devices 102 are deployed within the aortic cuff 1464 after the cuff 1464 has been at least substantially sealed against the aortic neck 60. The superior portions 108 can mate with and substantially seal to the interior of the aortic cuff 1464. The ribs 530 of the cover 106 can interface with the interior surface of the sleeve 1466 to further strengthen the seal. Additionally, the integrated frame 104 can further improve the seal between the endograft devices 102 and the aortic cuff 1464. For example, the cross-section of the frame 104 in the expanded configuration can be slightly larger than an interior cross-section of the aortic cuff 1464. As the endograft devices 102 are deployed within the aortic cuff 1464, the radial forces from the expansion of the endograft devices 102 can strengthen the seal therebetween. Additionally, in some embodiments, the transition portion 324 of the endograft devices can mate with a complementary taper within the aortic cuff 1464.

In some embodiments in accordance with the technology, the aortic cuff 1464 can include alignment aids, such as the alignment aids 734 described above with reference to FIGS. 7A and 7B, to facilitate positioning the endograft devices 102 within the aortic cuff 1464. For example, the aortic cuff 1464 and the outer walls 112 of the endograft devices 102 can include orthogonal alignment aids that intersect to indicate the endograft devices 102 are properly aligned within the aortic cuff 1464.

In additional embodiments, the aortic cuff 1464 can include anchors, such as the anchors 836 described above with reference to FIGS. 8A and 8B, to secure the to secure the system 1400 in situ. For example, the cuff frame 1468 can include anchors that project radially outwardly and engage adjacent arterial walls.

FIGS. 15A and 15B are schematic views of a three-part modular endograft system 1500 ("system 1500") being deployed across the aneurysm 50 in accordance with an embodiment of the technology. The system 1500 can include the endograft devices 102 described with respect to the system 100 and the aortic cuff 1464 described above with reference to FIGS. 14A and 14B.

Referring to FIG. 15A, the delivery system 40 can be inserted using a generally similar method as described above with reference to FIG. 9A. In the embodiment shown in FIG. 15A, however, the first catheter 42a and the first guidewire 44a can be inserted first to. deliver the aortic cuff 1464 (FIG. 15B) to the target site T. The aortic cuff 1464 can be deployed using a generally similar method as deploying the endograft devices 102 described above with reference to FIGS. 9A and 9B. The first guidewire 44a can be used to adjust the aortic cuff 1464 to a desired position in the aortic neck 60.

As shown in FIG. 15B, the endograft devices 102 can be deployed within the aortic cuff 1464. The endograft devices 102 can be deployed using a substantially similar method as described with reference to FIG. 9B. For example, the endograft devices 102 can be delivered through the first and second catheters 42 and positioned independently within the aortic cuff 1464 using the guidewires 44. Similar to the method of deploying the superior portions 108 directly against the arterial walls described with reference to FIGS. 9B and 13B, here the outer walls of the superior portions 108 can at least partially interface with the interior surface of the aortic cuff 1464 such that the septal walls are aligned with each other to form the septum 120 (not visible). In some embodiments in accordance with the technology, the aortic cuff 1464 can include sections shaped to receive the endograft devices 102 and thereby ease alignment. In further embodiments, the first endograft device 102a can be anchored or otherwise secured to the aortic cuff 1464 before deployment such that only the second endograft device 102b must be positioned within the aortic cuff 1464.

Figure 16:
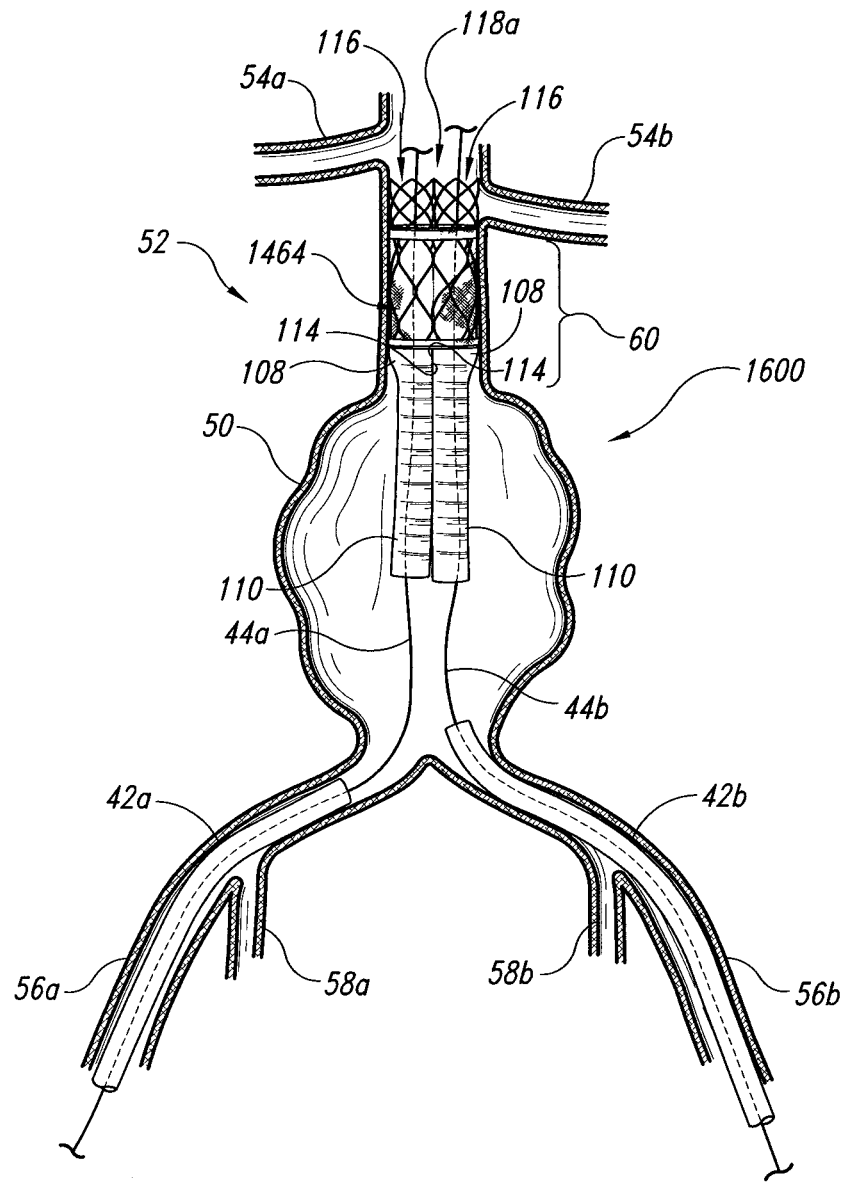
FIG. 16 is a schematic view of a five-part modular endograft system being deployed across an aneurysm in accordance with an embodiment of the technology.

FIG. 16 is a schematic view of a modular endograft system 1600 ("system 1600") being deployed across the aneurysm 50 in accordance with another embodiment of the technology. The system 1600 can be deployed using generally similar methods as the system 1500 described above with reference to FIGS. 15A and 15B. As shown in FIG. 16, however, the superior portions 108 project above the aortic cuff 1464 such that the first end portions 118a provide additional structure for securing the endograft devices to the arterial walls of the aorta 52. Additionally, the inferior portions 110 of the endograft devices 102 terminate within the aneurysm 50. Therefore, the system 1600 further includes limbs (not shown), such as the limbs 1362 described above with reference to FIGS. 13A-C, that connect to the inferior portions 110 and extend into the iliac arteries 56. The catheters 42 can be used to adjust the length of the limbs to accommodate differing anatomies of the iliac arteries 56 and to maximize the fixation and sealing areas between the limbs and the arterial walls. Additionally, in some embodiments, the limbs can intersect (e.g., the limbs 1362 shown in FIG. 13C) to strengthen the seal at the aortic neck 60 and decrease the likelihood of endoleaks. Similar to the four-part system 1300 described above, the five-part system 1600 can accommodate anatomical variations without requiring customized components.

In the embodiments illustrated in FIGS. 9A, 9B, 11-13C, 15A, 15B and 16, the aneurysm 50 is shown in the infrarenal portion of the aorta 52 because this is the most common site of an AAA. In other embodiments in accordance with the technology, the modular endograft systems 100, 1000, 1300, 1500 and 1600 can be deployed across aneurysms 50 at different portions of the aorta 52 or in other vessels altogether. For example, in some embodiments, the aneurysm 50 can extend from the infrarenal portion of the aorta 52 into one or both of the common iliac arteries 56. The inferior portions 110 or the limbs 1362 of the systems 100, 1000, 1300, 1500 and 1600 can extend past the diseased, aneurysmal portion of the iliac arteries 56 without blocking blood flow to the internal iliac arteries 58. In other embodiments, the systems 100, 1000, 1300, 1500 and 1600 can be deployed across aneurysms 50 located in the supra renal portion of the aorta 52 with the fenestrations 1038 and/or the first end portions 118a positioned at the entrance of the renal arteries 54. In further embodiments, the systems described above can be deployed across aneurysms in other portions of the vasculature that benefit from the use of a bifurcated, bi-luminal modular endograft system that can be independently positioned.

4. Methods of Manufacturing 4.1 Integrated Frame

Referring back to FIGS. 4A and 4B, the integrated frame 104 can be made by weaving or braiding one continuous wire 426 in a pattern along a cylindrical mandrel. In some embodiments, the wire 426 is woven with a one over and one under pattern. In other embodiments, the wire 426 is woven with a two over and one under pattern, another integrated pattern, and/or a pattern that varies over the length of the frame 104. The intersections of the wire 426 can remain unbound to increase flexibility of the frame 104. The wire 426 can form the loops 428 to change direction and continue the pattern of intersecting wires 426. As described above, the number of loops 428 at each end portion 118 and the braid angle a can be selected based on the diameter of the wire 426 and the desired properties of the frame 104.

The wire 426 can be removed from the mandrel after it is braided into the frame 104 and formed into a desired shape (e.g., the endograft devices 102 shown above). The frame 104 can then be heated to a shape-setting temperature specified for the wire material (e.g., Nitinol), and subsequently quenched. Optionally, the frame 104 can be annealed to increase the strength of the frame 104. The mandrel can be cylindrical or have the shape of the frame 104 such that the wire 426 remains on the mandrel during heat treatment. In further embodiments, the frame 104 can be manufactured using other suitable methods for shaping resilient biocompatible materials.

4.2 Covers and Coatings

Referring to FIGS. 5A-C, the cover 106 can be made by shaping a substantially non-permeable cover material, such as Dacron®, PTFE, and/or other suitable biocompatible materials. The cover 106 can be formed by first placing the cover material over a mandrel. The mandrel can include thin grooves that can correspond to the desired geometry of the ribs 530 on the cover 106. A wire or thread can be wrapped over the cover material and into the grooves to corrugate the cover material. The cover material can then be heated on the mandrel until the ribs 530 are formed and the cover 106 is substantially non-permeable. In some embodiments, the superior and inferior termini 531a and 531b of the cover 106 can be shaped to facilitate attaching the cover 106 to a frame (e.g. the frame 104 shown in FIGS. 4A and 4B) and prevent the cover 106 from wrinkling at end portions (e.g., the end portions 118 shown in FIGS. 1A and 1B) during constriction. For example, the superior and inferior termini 531a and 531b can be zigzagged as shown in FIGS. 5A and 5B, scalloped, or otherwise shaped to limit wrinkling of the cover on the frame.

In other embodiments in accordance with the technology, coating layers can be used in place of or in conjunction with the cover 106. FIGS. 17A-E are views of coating layers being applied to an integrated frame 1704 ("frame 1704") in accordance with embodiments of the technology. The frame 1704 has generally similar features as the frame 104 described above. For example, the frame 1704 can be made from the braided wire 426.

Referring to FIG. 17A, the frame 1704 is positioned over a mandrel 80 in the expanded configuration. As shown in FIG. 17A, a first coating layer 1770 can be wrapped onto the frame 1704. The first coating layer 1770 can be a single or double layer of unsintered tape that can be approximately 0.0005" thick and made from PTFE. In other embodiments, the first coating layer 1770 can have a different thickness and/or the first coating layer 1770 can be made from another suitable coating material.

Once the first coating layer 1770 is applied over the frame 1704, the first coating layer 1770 and the frame 1704 can be heated on the mandrel 80 in an oven. For example, the first coating layer 1770 and the frame 1704 can be heated for less than thirty minutes in a 370° C. oven. After heating, the coated frame 1704 is removed from the mandrel 80 and extended and contracted from the low-profile configuration to the expanded configuration to ensure the first coating layer 1770 properly adhered to the frame 1704 during heat treatment.

As shown in FIG. 17B, a second coating material 1772 is placed over a narrower, second mandrel 82. The second coating material 1772 can be extended a distance equivalent to the length of the frame 1704 in the low-profile configuration. Referring to FIG. 17C, the second coating material 1772 is contracted to the length of the frame 1704 in the expanded configuration. This contraction can form small ribs 1730 in the second coating material 1772. The ribs 1730 can be generally similar to the ribs 530 described above with reference to FIGS. 5A-C, but they are on the interior of the frame 1704. The ribs 1730 prevent the second coating material 1772 from wrinkling or bunching when the subsequently attached frame 1704 flexes or bends and thereby reduce the likelihood of thrombotic problems within the lumen.

Figure 17D:
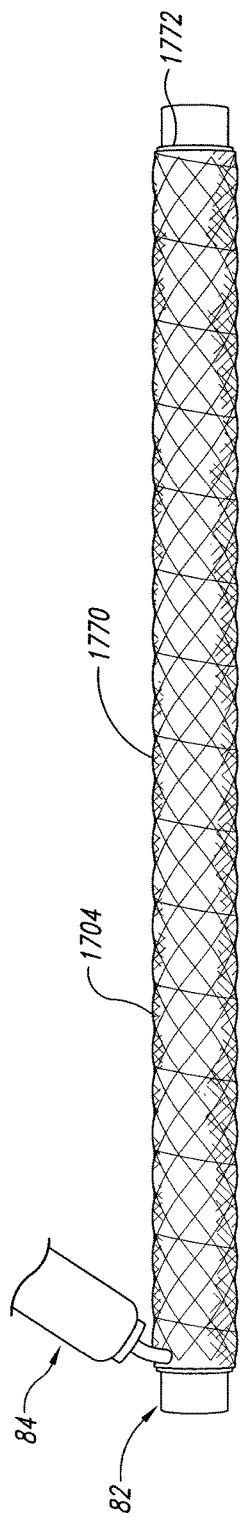
Figure 17E:
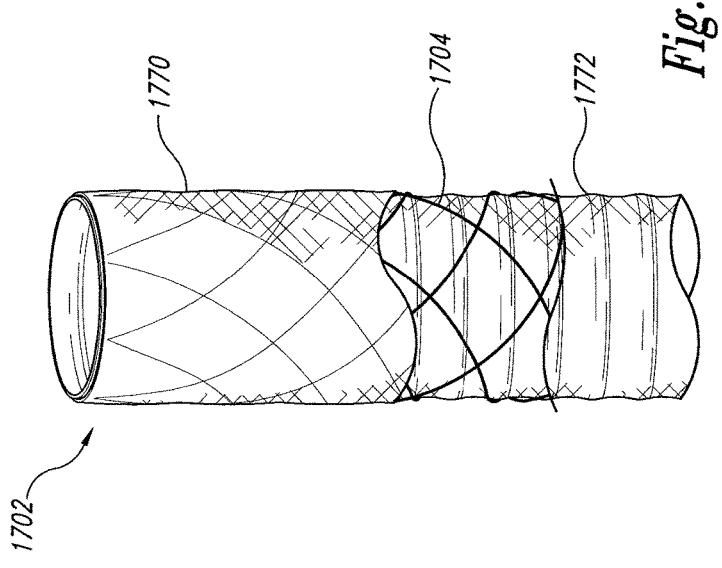

As shown in FIG. 17D, the coated frame 1704 is then extended to the low-profile configuration and placed over the extended second coating material 1772 on the second mandrel 82. Each diamond opening along the frame 1704 can be spot welded using a welding device 84. Then, the frame 1704 is removed from the second mandrel 82 and extended and contracted from the low-profile configuration to the expanded configuration to ensure that the first and second coating layers 1770 and 1772 have adequately adhered to the frame 1704. Additionally, the proximal and distal ends of the frame 1704 are verified to ensure that the first and second coating layers 1770 and 1772 have properly adhered to the frame 1704. If necessary, tacking can be performed and the edges can be trimmed to form a dual coated endograft device 1702 shown in FIG. 17E.

From the foregoing, it will be appreciated that specific embodiments of the invention have been described herein for purposes of illustration, but that various modifications may be made without deviating from the spirit and scope of the technology. For example, the embodiments illustrated in FIGS. 1A-16 include covers 106 that extend over the exterior of the integrated frames 104. However, other embodiments of the technology can include covers 106 that are attached to the interior of the integrated frame 104 and/or are formed integrally with the frame 104. Certain aspects of the new technology described in the context of particular embodiments may be combined or eliminated in other embodiments. For example, in the embodiments illustrated above, each endograft device (e.g., 102, 1002) includes a singular lumen 116. However, the endograft devices can include additional lumens that transverse, bisect, and/or otherwise communicate with the lumen 116 to accommodate the vasculature. For example, the endograft devices can include lumens that extend into the renal arteries, the internal iliac arteries, and/or other arteries. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of repairing an aneurysm in an aorta of a human patient, the method comprising:
    advancing a first endograft device to a target site in the aorta before the aneurysm, wherein the first endograft device includes a first frame, a first cover, and a first lumen within the first cover, wherein the first frame and the first cover have a first superior portion and a first inferior portion, the first superior portion having a first outer wall and a first septal wall that together define a substantially D-shaped cross-section;
    advancing a second endograft device to the target site in the aorta, wherein the second endograft device includes a second frame, a second cover, and a second lumen within the second cover, wherein the second frame and the second cover have a second superior portion and a second inferior portion, and the second superior portion having a second outer wall and a second septal wall that together define a substantially D-shaped cross-section, wherein the first and second endograft devices are positioned independently of one another;
    longitudinally staggering a superior end of the first septal wall of the first frame of the first endograft device with respect to a superior end of the second septal wall of the second frame of the second endograft device within the aorta to accommodate the naturally anatomically variable orientation of renal arteries of the patient; and
    deploying the staggered first and second endograft devices at the target site such that the first and second endograft devices self-expand to an expanded configuration via inherent hoop forces in the first and second frames, wherein after deployment the first and second septal walls press against each other to form a septum between the first and second lumens with the superior ends of the first and second septal walls longitudinally staggered, and wherein the first and second outer walls press against a vessel wall of the aorta.

2. The method of claim 1, further comprising:
    percutaneously introducing the first endograft device into the aorta via a first blood vessel; and
    percutaneously introducing the second endograft device into the aorta via a second blood vessel different than the first blood vessel.

3. The method of claim 1 wherein the first and second endograft devices have a cross-sectional dimension no less than 20 mm in the expanded configuration, and wherein the first and second catheters are no larger than 14 F.

4. The method of claim 1 wherein the first cover includes first ribs on the first septal wall and the second cover includes second ribs at the second septal wall, and wherein:
    deploying the first and second endograft devices further comprises transforming the first and second ribs from a low-profile configuration with a first length and a first diameter to an expanded configuration with a second length shorter than the first length and a second diameter greater than the first diameter,
    wherein the first and second ribs are arranged circumferentially about longitudinal axes of the first and second frames and, when deployed, project outwardly from the first and second frames, respectively, such that the first and second ribs mate with each other along the first and second septal walls.

5. The method of claim 1 wherein the first cover attaches over at least a portion of the first frame, the second cover attaches over at least a portion of the second frame, and deploying the first and second endograft devices further comprises:
    restricting radial expansion of the first frame with the first cover; and
    restricting radial expansion of the second frame with the second cover.

6. The method of claim 1 wherein the first cover includes an opening defined within, and entirely bounded by, the first outer wall of the first superior portion, and wherein deploying the first and second endograft devices further comprises:
    positioning the opening at an entrance of a renal artery of the patient, the renal artery having transverse fluid flow relative to a longitudinal axis of the aorta, and wherein the opening allows blood to flow through the first lumen and to the renal artery.

7. The method of claim 1 wherein longitudinally staggering the ends of the first and second frames comprises longitudinally offsetting the superior end of the first frame from the superior end of the second frame by at least 5 mm.

8. The method of claim 1 wherein longitudinally staggering the ends of the first and second frames comprises treating an abdominal aortic aneurysm proximal to a short aortic neck by forming a sealing area between the first outer wall and the aorta that is larger than a sealing area of the second outer wall and the aorta.

9. The method of claim 1 wherein:
    the first cover of the first frame is defined by a single layer of first cover graft material, wherein the first cover has a first cover outer surface and a first cover inner surface with the first cover graft material extending continuously therebetween;
    the second cover of the second frame is defined by a single layer of second cover graft material, wherein the second cover has a second cover outer surface and a second cover inner surface with the second cover graft material extending continuously therebetween;
    the first cover outer surface substantially conforms to the first frame when the first frame is in an expanded state;
    the second cover outer surface substantially conforms to the second frame when the second frame is in an expanded state; and
    the first and second covers contact each other at the first and second septal walls.

10. The method of claim 1 wherein longitudinally staggering the ends of the first and second frames comprises longitudinally offsetting the superior end of the first cover from the superior end of the second cover by at least 5 mm.

11. The method of claim 1 wherein:
    the step of advancing the first endograft device to the target site includes simultaneously advancing the first frame and the first cover together, and
    the step of advancing the second endograft device to the target site includes simultaneously advancing the second frame and the second cover together.

12. The method of claim 1 wherein the first endograft device includes a first alignment aid at the first septal wall, wherein the second endograft device includes a second alignment aid at the second septal wall, the first and second alignment aids comprising a radiopaque material, and wherein deploying the first and second endograft devices further includes:
    radiographically positioning the first and second alignment aids such that the first and second alignment aids are opposite another;
    viewing the first and second alignment aids in the orthogonal plane; and
    crossing the first and second alignment aids such that the first and second septal walls can form the septum.

13. The method of claim 12 wherein the first and second alignment aids diagonally cross the first and second septal walls, respectively, and wherein crossing the first and second alignment aids forms an "X" indicator.

14. A method of treating an abdominal aortic aneurysm (AAA) of a human patient, the method comprising:
    positioning a first endograft device in an abdominal aorta of the patient relative to the aneurysm such that at least a segment of a first superior portion of the first endograft device is positioned superior to the aneurysm and a first inferior portion of the first endograft device extends at least partially through the aneurysm, wherein the first superior portion comprises a first braided frame with a convexly curved first outer wall and a first septal wall that define a substantially D-shaped cross-section, with at least a portion of the first braided frame having a first cover extending about the circumference of the first braided frame;
    positioning a second endograft device in the abdominal aorta of the patient relative to an aneurysm such that at least a segment of a second superior portion of the second endograft device is positioned superior to the aneurysm and longitudinally offset relative to the first braided frame of the first endograft device, and such that a free end portion of the first braided frame projects distally beyond the superior end of the second endograft device, wherein—
    a second inferior portion of the second endograft device extends at least partially through the aneurysm,
    the second superior portion comprises a second braided frame with a convexly curved second outer wall and a second septal wall that define a substantially D-shaped cross-section, the second braided frame defining the superior end of the second endograft device, with at least a portion of the second braided frame having a second cover extending about the circumference of the second braided frame, and
    the second endograft device is positioned independently of the first endograft device;
    deploying the first endograft device from a first catheter and deploying the second endograft device from a second catheter such that the first and second superior portions self-expand to an expanded configuration in which the first and second septal walls press against each other via an inherent spring force to form a septum between the first and second lumens, wherein the free end portion of the first braided frame projecting distally beyond the superior end of the second superior portion at least substantially maintains the substantially D-shaped cross-section, and wherein the septal wall of the first braided frame has the first cover thereon, the septal wall and its first cover projecting distally beyond the superior end of the second endograft device and its second cover after the first and second endograft devices are deployed.

15. The method of claim 14 wherein the first septal wall is convexly curved in a direction opposite the first outer wall and the second septal wall is convexly curved in a direction opposite the second outer wall, and wherein deploying the first and second endograft devices comprises urging the convexly curved first and second septal walls together.

16. The method of claim 14 wherein:

the first catheter has a maximum cross-sectional dimension of 5 mm and the first outer wall of the first superior portion of the first endograft device has a radius of curvature not less than 10 mm after being deployed from the first catheter; and the second catheter has a maximum cross-sectional dimension of 5 mm and the second outer wall of the second superior portion of the second endograft device has a radius of curvature not less than 10 mm after being deployed from the second catheter.

17. The method of claim 14 wherein:

the first endograft device has a first cover attached to a portion of the first braided frame, the first cover having a first opening at the first outer wall;

the second endograft device has a second cover attached to the second braided frame, the second cover having a second opening at the second outer wall, wherein the first and second openings allow blood to flow laterally relative to a longitudinal axis of the first lumen and second lumen; and deploying the first and second endograft devices comprises positioning the first end portion of the first braided frame at the entrance of a first renal blood vessel of the patient and positioning the first end portion of the second braided frame at the entrance of a second renal blood vessel of the patient longitudinally offset from the first renal blood vessel, and wherein the first and second endograft devices are staggered with respect to a longitudinal axis of the abdominal aorta in a manner to approximate the offset between the first and second renal arteries of the patient.

18. The method of claim 14, further comprising:

positioning a first limb such that a distal portion of the first limb is coupled to the first inferior portion of the first endograft device and a proximal portion of the first limb is in a first iliac artery of the patient; and positioning a second limb such that a distal portion of the second limb is coupled to the second inferior portion of the second endograft device and a proximal portion of the second limb is in a second iliac artery of the patient.

19. The method of claim 14 wherein:

the first endograft has a first cover on the first braided frame, the first cover having a single layer of material;

the second endograft has a second cover on the second braided frame, the second cover having a single layer of material; and the first and second covers press against each other at the septum.

20. The method of claim 14 wherein the first cover of the septal wall of the first braided frame projects distally beyond the second cover of the second endograft device by at least 5 mm.

21. The method of claim 14 wherein:

the step of positioning the first endograft device includes simultaneously positioning the first braided frame and the first cover together, and the step of advancing the second endograft device includes simultaneously positioning the second braided frame and the second cover together.

22. A method of treating an aneurysm in an abdominal aorta of a human patient, the method comprising:

positioning a superior portion of a first endograft device in the aorta between the aneurysm and a first renal artery of the patient, wherein the superior portion of the first endograft device has a substantially D-shaped cross-section;

positioning a superior portion of a second endograft device in the aorta between the aneurysm and a second renal artery of the patient offset from the first renal artery of the patient, wherein the superior portion of the second endograft device has a substantially D-shaped cross-section;

sealing an outer wall of the superior portion of the first endograft device to a first portion of the aorta at least partially superior to the second renal artery of the patient and inferior to the first renal artery of the patient;

sealing an outer wall of the superior portion of the second endograft device to a second portion of the aorta offset from the first portion of the aorta and inferior to both the first and second renal arteries of the patient, wherein the first and second endograft devices each comprise a braided stent extending from a superior end to an inferior end of the corresponding endograft device, with the superior portions of the first and second endograft devices having covers extending from their superior ends and circumferentially enclosing the braid of the braided stent; and sealing a septal wall of the superior portion of the first endograft device to a septal wall of the superior portion of the second endograft device such that a superior end of the septal wall of the first endograft device is longitudinally offset from a superior end of the septal wall of the second endograft when the outer walls of the superior portions of the first and second endograft devices are sealed to their respective first and second portions of the aorta.

23. The method of claim 22, further comprising:

advancing the first and second endograft devices to the aorta in a low-profile configuration, wherein the first and second endograft devices each comprise a braided frame having at least one anchor integrated with the braided frame such that the anchor retracts against the braided frame in the low-profile configuration; and deploying the first and second endograft devices to an expanded configuration, wherein, upon expansion of the braided frames, the anchors self-deploy and project outwardly from the braided frames.

24. The method of claim 22 wherein:

the first endograft comprises a first cover on the braided frame of the first endograft device;

the second endograft comprises a second cover on the braided frame of the second endograft device;

the first and second covers each have a single layer of material; and the first and second covers are sealed together at the septal walls of the superior portions of the first and second endograft devices.

25. The method of claim 22 wherein the cover of the first endograft device projects distally beyond the cover of the second endograft device by at least 5 mm.

26. The method of claim 22 wherein:
the step of positioning the superior portion of the first endograft device includes simultaneously positioning the braided stent and cover of the first endograft device together as a unit, and
the step of positioning the superior portion of the second endograft device includes simultaneously positioning the braided stent and cover of the second endograft device together as a unit.

27. A method of treating an aneurysm in an aorta of a human patient, the method comprising:
positioning at least a segment of a first superior portion of a first endograft device in the aorta before the aneurysm, wherein the first superior portion has a substantially D-shaped cross-section, and wherein the first endograft device comprises—
a first braided frame extending from a superior end of the first endograft device to an inferior end of the first endograft device, and
a first cover on the first braided frame, the first cover circumferentially enclosing at least a portion of the first braided frame and having an outer surface that substantially conforms to the first braided frame when the first braided frame is in an expanded state;
positioning at least a segment of a second superior portion of a second endograft device in the aorta before the aneurysm, wherein the second superior portion has a substantially D-shaped cross-section, and wherein the second endograft device comprises—
a second braided frame extending from a superior end of the second endograft device to an inferior end of the second endograft device, and
a second cover on the second braided frame, the second cover circumferentially enclosing at least a portion of the second braided frame and having an outer surface that substantially conforms to the second braided frame when the second braided frame is in an expanded state;
at least partially deploying the first superior portion of the first endograft device within the aorta, wherein, during deployment, the first endograft device expands to a first cross-sectional area via inherent outward spring force of the first braided frame;
constricting the first superior portion of the first endograft device to a second cross-sectional area less than the first-cross sectional area;
repositioning the first superior portion within the aorta while the first superior portion is constricted to the second cross-sectional area;
deploying the first superior portion of the first endograft device within the aorta after constriction; and
deploying the second superior portion of the second endograft device within the aorta such that the first and second superior portions form a sealed septum between the first and second endograft devices, and such that the first cover of the first endograft device at the septum extends superior to the second cover of the second endograft device at the septum after deployment.

28. The method of claim 27 wherein the first cover of the first endograft device extends superior to the second cover of the second endograft device by at least 5 mm.

29. The method of claim 27 wherein:
the step of positioning at least a segment of the first superior portion of the first endograft device includes simultaneously positioning the first braided frame and the first cover together; and
the step of positioning at least a segment of the second superior portion of the second endograft device includes simultaneously positioning the second braided frame and the second cover together.

30. A method of treating an aneurysm in an aorta of a human patient, the method comprising:
advancing a first endograft device through a left iliac artery of the patient;
advancing a second endograft device through a right iliac artery of the patient;
positioning a first superior portion of the first endograft device in the aorta proximate a right renal artery of the patient;
positioning a second superior portion of the second endograft device in the aorta proximate a left renal artery of the patient such that the first and second endograft devices cross each other within the aorta;
deploying the first endograft device such that at least a segment of the first superior portion seals with a right portion of the aorta proximate the right renal artery and a first inferior portion of the first endograft device seals to a portion of the left iliac artery; and
deploying the second endograft device such that at least a segment of the second superior portion seals with a left portion of the aorta proximate the left renal artery and a second inferior portion of the second endograft devices seals to a portion of the right iliac artery, and such that the second endograft device abuts the first at a septum, with one of the first and second endograft devices extending superiorly beyond the other of the first and second endograft devices at the septum after deployment.

31. A method of treating an aneurysm in an aorta of a human patient, the method comprising:
positioning a first superior portion of a first endograft device in the aorta proximate to the aneurysm, wherein the first superior portion has a first frame and a first graft material over the first frame, and wherein the first superior portion has a substantially D-shaped cross-section defined by a convexly curved first outer wall and a first septal wall;
positioning a second superior portion of a second endograft device in the aorta proximate to the aneurysm, wherein the second superior portion has a second frame and a second graft material over the second frame, and wherein the second superior portion has a substantially D-shaped cross-section defined by a convexly curved second outer wall and a second septal wall;
longitudinally staggering a superior terminus of the first graft material and a superior terminus of the second graft material such that the superior termini of the first and second graft material are longitudinally offset from each other along the first and second septal walls; and
sealing the longitudinally staggered first and second graft materials together at the first and second septal walls to form a sealed septum wherein the superior termini of the first and second graft material are longitudinally offset from each other along the first and second septal walls after the first and second graft materials are sealed together at the first and second septal walls.

32. The method of claim 31 wherein:
the first graft material substantially conforms with the first frame when the first frame is in an expanded state; and
the second graft material substantially conforms with the second frame when the second frame is in the expanded state.

33. The method of claim 31 wherein the superior termini of the first and second graft material are longitudinally offset from each other along the first and second septal walls by at least 5 mm.

34. The method of claim 31 wherein:
the step of positioning the first superior portion of the first endograft device includes simultaneously positioning the first frame and the first graft material together; and
the step of positioning the second superior portion of the second endograft device includes simultaneously positioning the second frame and the second graft material together.

\* \* \* \* \*